US008735146B2

(12) United States Patent
McGregor

(10) Patent No.: US 8,735,146 B2
(45) Date of Patent: *May 27, 2014

(54) CHIMERIC BINDING PEPTIDE LIBRARY SCREENING METHOD

(75) Inventor: Duncan McGregor, Oldemeldrum (GB)

(73) Assignee: The University Court of the University of Aberdeen (GB)

( * ) Notice: Subject to any disclaimer, the term of this patent is extended or adjusted under 35 U.S.C. 154(b) by 1125 days.

This patent is subject to a terminal disclaimer.

(21) Appl. No.: 11/985,355

(22) Filed: Nov. 13, 2007

(65) Prior Publication Data

US 2008/0220981 A1    Sep. 11, 2008

Related U.S. Application Data

(63) Continuation of application No. 09/486,882, filed as application No. PCT/GB98/02630 on Sep. 2, 1998, now Pat. No. 7,312,074.

(30) Foreign Application Priority Data

Sep. 2, 1997    (GB) .................................. 9718455.0

(51) Int. Cl.
*C12N 15/00* (2006.01)
*C12Q 1/68* (2006.01)
(52) U.S. Cl.
USPC .......................... 435/320.1; 435/6.1; 435/7.1
(58) Field of Classification Search
None
See application file for complete search history.

(56) References Cited

U.S. PATENT DOCUMENTS

| 5,270,170 | A  | 12/1993 | Schatz et al. ................. 435/7.37 |
| 5,403,484 | A  | 4/1995  | Ladner et al. ............... 435/235.1 |
| 5,498,530 | A  | 3/1996  | Schatz et al. ................. 435/69.1 |
| 5,597,693 | A  | 1/1997  | Evans et al. ........................ 435/6 |
| 6,451,527 | B1 | 9/2002  | Larocca et al. .................... 435/6 |

FOREIGN PATENT DOCUMENTS

| DE | 196 46 372 C1 | 11/1996 |
| WO | PCT/GB91/01134 | 7/1991 |
| WO | PCT/GB92/00883 | 5/1992 |
| WO | PCT/US92/08879 | 10/1992 |

OTHER PUBLICATIONS

Hannenhalli et al (2008 Bioinformatics Advance Access pp. 1-8).*
Hanes et al (1997 PNAS 94:4937-4942).*
Wilson et al (1991 Annu. Rev. Genet. 25:585-627).*
Turpen et al (1995 Nature Biotechnology 13:53-57).*

(Continued)

*Primary Examiner* — Samuel Woolwine
*Assistant Examiner* — Kaijiang Zhang
(74) *Attorney, Agent, or Firm* — Charles N. Quinn; Fox Rothschild LLP

(57) ABSTRACT

There is described a method of isolating nucleotide sequences encoding target peptides from DNA libraries using DNA binding proteins to link the peptide to the sequence which encodes it. DNA libraries are prepared from cells encoding the protein of interest, or from synthetic DNA, and inserted into, or adjacent to, a DNA binding protein in an expression vector to create a chimeric fusion protein. Incorporation of the vector DNA into a carrier package, during expression of the chimeric fusion protein, results in the production of a peptide display carrier package (PDCP) displaying the DNA-bound fusion protein on the external surface of the carrier package. Employment of affinity purification techniques results in the PDCP particles containing sequences encoding the desired peptide to be selected and the desired nucleotide sequences obtained therefrom.

7 Claims, 9 Drawing Sheets

(56) References Cited

OTHER PUBLICATIONS

Barbas, C.F. and Burton, D.R., Selection and evolution of high-affinity human anti-viral antibodies. Trends Biotechnol. 14:230-234 (1996) (abstract only).
Brown, Miles & Sharp, Phillip A., *Human Estrogen Receptor Forms Multiple Protein-DNA Complexes*, The Journal of Biological Chemistry, vol. 265, No. 19, pp. 11238-11243 (1990).
Burritt, J.B. et al., Antibody imprint of a membrane protein surface. Phagocyte flavocytochrome b. J. Biol. Chem. 273:24847-24852 (1998) (abstract only).
Cull et al., Screening for receptor ligands using large libraries of peptides linked to the C terminus of the lac repressor. PNAS 89:1865-1869 (1992).
Davies, J. and Riechmann, L., Single antibody domains as small recognition units: design and in vitro antigen selection of camelized, human VH domains with improved protein stability. Protein Eng. 9:531-537 (1996) (abstract only).
Engberg, J. et al., Phage-display libraries of murine and human antibody Fab fragments. Mo. Biotechnol. 6:287-310 (1996) (abstract only).
Fakhfakh, F. et al., Antibody epitopes probed by immunoselected phage-display library peptides in members of a family with various rheumatic manifestations. Clin. Exp. Rheumatol. 14:607-611 (1996) (abstract only).
Franceschi., *Proc Natl Acad Sci* USA, 1984 81(8):2337-41 "Interaction of the 1 alpha, 2,5-dihydroxyvitamin D3 receptor with RNA and synthetic polyribonucleotides" (Abstract).
Gawyer, C. et al., Methodology for selection of human antibodies to membrane proteins from a phage-display library. J. Immunol. Methods 26:193-203 (1997) (abstract only).
Germaschewski, V. and Murray, J., Identification of polyclonal serum specificities with phage-display libraries. J. Virol. Methods 189:73-82 (1996) (abstract only).
Hughes-Jones, N.C. et al., Characterization of human blood group scFv antibodies derived from a V gene phage-display library. Br. J. Haematol. 88:180-186 (1994) (abstract only).
Hughes MR et al., *Biochemistry*, 1981 20(9):2481-91 "Interaction of the chick oviduct progesterone receptor with deoxyribonucleic acid" (Abstract).
Smith J.W. et al., Building synthetic antibodies as adhesive ligands for integrins. J. Biol. Chem. 269:32788-32795 (1994) (abstract only).
Lang, I.M. et al., Recombinant rabbit Fab with binding activity to type-1 plasminogen activator inhibitor derived from a phage-display library against human alpha-granules. Gene 172:295-298 (1996) (abstract only).
Sozeri et al., *Nucleic Acid Res* 1992 20(9):2257-63 "Determination of the DNA sequence recognized by the bHLH-zip domain of the N-Myc protein" (Abstract).
Thiesen et al., *Nucleic Acid Res* 1990 18(11):3203-9 "Target Detection Assay (TDA): a versatile procedure to determine DNA binding sites as demonstrated on SP1 protein" (Abstract).
Lin SY et al., *Biochim, Biophys Acta* 1981 654(2):181-6 "The binding of androgen receptor to DNA and RNA" (Abstract).
McCafferty, J. et al., Selection and rapid purification of murine antibody fragments that bind a transition-state analog by phage display. Appl. Biochem Biotechnol. 47:157-171 (1994) (abstract only).
Meulemans, E.V. et al., Selection of phage-displayed antibodies specific for a cytoskeletal antigen by competitive elution with a monoclonal antibody. J. Mol. Biol. 244:353-360 (1994) (abstract only).
Norby et al., *Nucleic Acid Res* 1992 20(23): 6317-21 "Determination of recognition-sequences for DNA-binding proteins by a polymerase chain reaction assisted binding site selection method (BSS) using nitrocellulose immobilized DNA binding protein" (Abstract).
Pierrou et al., *Anal Biochem* 1995 229(1):99-105 "Selection of high affinity binding sites for sequence-specific, DNA binding proteins from random sequence oligonucleotides" (Abstract).

Sasano, M. et al., Molecular selection of human antibodies with an unconventional bacterial B cell antigen. J. Immunol. 151:5822-5839 (1993) (abstract only).
Walker, J. and Banting, G., Production of phage-display antibodies for epitope mapping. Methods Mol. Biol. 66:391-405 (1996) (citation only).
Robert A. Coleman and B. Franklin Pugh, Evidence of Functional Binding and Stable Sliding of the TATA Binding Protein on Nonspecific DNA. J. Biol. Chem. 270:23, pp. 13850-13859 (1995).
Frances M.P. Wong et al., Cationic Lipid Binding to DNA: Characterization of Complex Formation. Biochemistry 35:18, pp. 5756-5763 (1996).
Yuan-Peng Zhang et al., Self-Assembling DNA-Lipid Particles for Gene Transfer. Pharmaceutical Research 14:2, pp. 190-196 (1997).
Purificacion Lopez-Garcia et al., Invitro DNA binding of the archeal protecin Sso7d indices negative supercoiling at temperatures typical for thermophilic growth. Nucleic Acids Research 26:10, pp. 2322-2328 (1998).
Weidanz, J.A. et al., Display of functional alphabeta single-chain T-cell receptor molecules on the surface of bacteriophage. J. Immunol. Methods 221:59-76 (1998) (abstract).
Noronha, E.J. et al., Limited diversity of human scFv fragments isolated by panning a synthetic phage-display scFv library with cultured human melanoma cells. J. Immunol. 161:2968-2976 (1998) (abstract).
Iba, Y. and Kurosawa, Y., Comparison of strategies for the construction of libraries of artificial antibodies. Immunol. Cell Biol. 75:217-221 (1997) (abstract).
Iba, Y. et al., Changes in the specificity of antibodies against steroid antigens by introduction of mutations into complementarity-determining regions of the V(H) domain. Protein Eng. 11:361-370 (1998) (abstract).
Jacobsson, J. and Frykberg, J., Gene VIII-based, phage-display vectors for selection against complex mixtures of libands. Biotechniques 24:294-301 (1998) (abstract).
Lamarre, A. and Talbot, P.J., Characterization of phage-displayed recombinant anti-idiotypic antibody fragments against coronavirus-neutralizing monoclonal antibodies. Viral. Immunol. 10:175-182 (1997) (abstract).
Petrenko, V.A. and Smith, G.P., Phages from landscape libraries as substitute antibodies. Protein Eng. 13:589-592 (2000) (abstract only).
Vitaliti, A. et al., Inhibition of tumor angiogenesis by a single-chain antibody directed against vascular endothelial growth factor. Cancer. Res. 60:4311-4314 (2000) (abstract only).
Lannigan et al., Estrogen receptor selectively binds the "coding strand" of an estrogen responsive element. PNAS 86:863-867 (1989).
Rebar et al., Zinc finger phage: affinity selection of fingers with new DNA binding specificities. Science 263:671-673 (1994).
Gearhart, et al., Inhibition of DNA binding by human estrogen-related receptor 2 and estrogen receptor alpha with minor groove binding polyamides. Biochemistry 44:4196-4203 (2005).
Irving, R.A. et al., Affinity maturation of recombinant antibodies using *E.coli* mutator cells. Immunotechnology 2:127-143 (1996) (abstract only).
Peterson, G. et al., Dissection of the ATP binding domain of the chaperone hsc70 for interaction with the coefactor Hap46. J. Biol. Chem. (2000) (abstract only).
Wright et al., *Mol Cell Biol* 1991 11(8):4104-10 "Cyclic amplification and selection of targets (CASTing) for the myogenin consensus binding site" (Abstract only).
Tyutyulkova, S. and Paul, S., Selection of functional human immunoglobulin light chains from a phage-display library. Appl. Biochem. Biotechnol. 47:191-197 (1994) (abstract only).
Silverman, G.J. et al., Superantigen properties of a human sialoprotein involved in gut-associated immunity. J. Clin. Invest. 96:417-426 (1995) (abstract only).
Ward, R.L. et al., Retrieval of human antibodies from phage-display libraries using enzymatic cleavage. J. Immunol. Methods 189:73-82 (1996) (abstract only).
Ferrieres G., et al., Dissection of the ATP binding domain of the chaperone hsc70 for interaction with the coefactor Hap46. J. Biol. Chem. (2000) (abstract only).

(56) References Cited

OTHER PUBLICATIONS

Mao, S., et al., Phage-display library selection of high-affinity human single-chain antibodies to tumor-associated carbohydrate antigens sialyl Lewisx and Lewisx. Proc. Natl. Acad. Sci USA 96:6953-6958 (1999) (abstract only).

Ivanenkov, V.V., et al., Targeted delivery of multivalent phage display vectors into mammalian cells. Biochim. Biophys. Acta 1448:463-472 (1999) (abstract only).

Burritt, J.B. et al., Topological mapping of neutrophil cytochrome b epitopes with phage-display libraries. *J. Biol. Chem.* 270:16974-16980 (1995) (abstract only).

Coleman, R., et al., Evidence of Functional Binding and Stable Sliding of the TATA Binding Protein on Nonspecific CAN, J. Biol Chem 270:23, pp. 18350-13859 (1995) (abstract only).

Lopez-Garcia, P., et al., In Vitro DNA binding of the archeal protecin Sso7d induces negative supercoiling at temperature typical for thermophilic growth, Nucleic Acids Research 26:10, pp. 2322-2328 (1998) (abstract only).

Zhang, Y., et al., Self-Assembling DNA-Lipid Particles for Gene transfer, Pharmaceutical Research 14:2, pp. 190-196 (1997) (abstact only).

Ferrieres G., et al., Affinity for the cognate monoclonal antibody of synthetic peptides derived from selection by phage display: Role of sequences Flanking the binding motif, J. Biol. Chem. 267: 1819-1829 (2000) (abstract only).

Coleman, R., et al., Evidence of Functional Binding and Stable Sliding of the TATA Binding Protein on Nonspecific CAN, J. Biol Chem 270:23, pp. 18350-13859 (1995) (full text).

Lopez-Garcia, P., et al., In Vitro DNA binding of the archeal protecin Sso7d induces negative supercoiling at temperature typical for thermophilic growth, Nucleic Acids Research 26:10, pp. 2322-2328 (1998) (full text).

Zhang, Y., et al., Self-Assembling DNA-Lipid Particles for Gene transfer, Pharmaceutical Research 14:2, pp. 190-196 (1997) (full text).

Wong, F., et al., Cationic Lipid Binding to DNA: Characterization of Complex Formation, Biochemistry 35:18, pp. 5756-5763, Dec. 1, 1995.

\* cited by examiner

Figure 1

```
1                              pelB
                               MET LYS TYR LEU LEU PRO THR ALA ALA ALA GLY LEU
AAGCTTGCATGCAAATTCTATTTCAAGGAGACAGTCATAA ATG AAA TAC CTA TTG CCT ACG GCA GCC GCT GGA TTG
TTCGAACGTACGTTTAAGATAAAGTTCCTCTGTCAGTATT TAC TTT ATG GAT AAC GGA TGC CGT CGA CGA CCT AAC
HindIII
77              SfiI                        PstI          NotI
        LEU LEU LEU ALA ALA GLN PRO ALA MET ALA GLU VAL GLN LEU GLN *** *** ALA ALA ALA
        TTA TTA CTC GCG GCC CAG CCG GCC ATG GCC GAG GTG CAA CTG CAG TAA TAG GCG GCC GCA
        AAT AAT GAG CGC CGG GTC GGC CGG TAC CGG GTC CAC GTC GAC GTC ATT ATC CGC CGG CGT 137                    ┌──────────────────────────────────────────────────────────→
        ┌─────────────────┐
        │GLY GLY GLY GLY SER│MET GLU SER ALA LYS GLU THR ARG TYR CYS ALA VAL CYS ASN ASP
        │GGG GGA GGA GGG TCC│ATG GAA TCT GCC AAG GAG ACT CGC TAC TGT GCA GTG TGC AAT GAC
        │CCC CCT CCT CCC AGG│TAC CTT AGA CGG TTC CTC TGA GCG ATG ACA CGT CAC ACG TTA CTG
        └─────────────────┘

197 ──────────────────────────────────────────────────────────────────────────────→
        TYR ALA SER GLY TYR HIS TYR GLY VAL TRP SER CYS GLU GLY CYS LYS ALA PHE PHE LYS
        TAT GCT TCA GGC TAC CAT TAT GGA GTC TGG TCC TGT GAG GGC TGC AAG GCC TTC TTC AAG
        ATA CGA AGT CCG ATG GTA ATA CCT CAG ACC AGG ACA CTC CCG ACG TTC CGG AAG AAG TTC

257 ──────────────────────────────────────────────────────────────────────────────→
        ARG SER ILE GLN GLY HIS ASN ASP TYR MET CYS PRO ALA THR ASN GLN CYS THR ILE ASP
        AGA AGT ATT CAA GGA CAT AAC GAC TAT ATG TGT CCA GCC ACC AAC CAG TGC ACC ATT GAT
        TCT TCA TAA GTT CCT GTA TTG CTG ATA TAC ACA GGT CGG TGG TTG GTC ACG TGG TAA CTA

317 ───────────── Oestrogen receptor DBD ─────────────────────────────────────────→
        LYS ASN ARG ARG LYS SER CYS GLN ALA CYS ARG LEU ARG LYS CYS TYR GLU VAL GLY MET
        AAA AAC AGG AGG AAG AGC TGC CAG GCC TGC CGG CTC CGT AAA TGC TAC GAA GTG GGA ATG
        TTT TTG TCC TCC TTC TCG ACG GTC CGG ACG GCC GAG GCA TTT ACG ATG CTT CAC CCT TAC 377 ──────────────────────────────────────────────────────────────────────────────→
        MET LYS GLY GLY ILE ARG LYS ASP ARG ARG GLY GLY ARG MET LEU LYS HIS LYS ARG GLN
        ATG AAA GGT GGG ATA CGA AAA GAC CGA AGA GGA GGG AGA ATG TTG AAA CAC AAG CGC CAG
        TAC TTT CCA CCC TAT GCT TTT CTG GCT TCT CCT CCC TCT TAC AAC TTT GTG TTC GCG GTC 437 ─────────────────────────┐
        ARG ASP ASP GLY GLU GLY ARG GLY GLU VAL GLY SER * *      HRE               EcoRI
        AGA GAT GAT GGG GAG GGC AGG GGT GAA GTG GGG TCT TGA TAA ┌TCAGGTCAGAGTGACCTGAGCTAAAATAACACATTCAG┐AATTC
        TCT CTA CTA CCC CTC CCG TCC CCA CTT CAC CCC AGA ACT ATT └AGTCCAGTCTCACTGGACTCGATTTTATTGTGTAAGTC┘TTAAG
```

Figure 3

Human Igk constant region

```
                                              K  R  T  V  A  A  P  S  V
                                              AAACGAACTGTGGCTGCACCATCTGTC
```

Clone #2
```
M  A↓Q  P  T  T  R  P  G  Q  G  T  R  L  D  I  K  R  T  V  A  A  P  S  V
ATGGCCCAGCCCACCACGCGTCCGGGCCAAGGGACACGACTGGACATTAAACGAACTGTGGCTGCACCATCTGTC
```

Clone #3
```
M  A↓Q  S  H  H  A  S  G  G  G  T  K  V  E  I  K  R  T  V  A  A  P  S  V
ATGGCCCAGTCCCACCACGCGTCCGGCGGAGGGACCAAGGTGGAGATCAAACGAACTGTGGCTGCACCATCTGTC
```

Human Igk constant region
```
F  I  F  P  P  S  D  E  Q  L  K  S  G  T  A  S  V  V  C  L  L  N  N  F  Y
TTCATCTTCCCGCCATCTGATGAGCAGTTGAAATCTGGAACTGCCTCTGTTGTGTGCCTGCTGAATAACTTCTAT
```

Clone #2
```
F  I  F  P  P  S  D  E  Q  L  K  S  G  T  A  S  V  V  C  L  L  N  N  F  Y
TTCATCTTCCCGCCATCTGATGAGCAGTTGAAATCTGGAACTGCCTCTGTTGTGTGCCTGCTGAATAACTTCTAT
```

Clone #3
```
F  I  F  P  P  S  D  E  Q  L  K  S  G  T  A  S  V  V  C  L  L  N  N  F  Y
TTCATCTTCCCGCCATCTGATGAGCAGTTGAAATCTGGAACTGCCTCTGTTGTGTGCCTGCTGAATAACTTCTAT
```

Figure 4

```
1HindIII                                          pelB
                                      MET LYS TYR LEU LEU PRO THR ALA ALA
AAGCTTGCAT GCAAATTCTA TTTCAAGGAG ACAGTCATAA ATG AAA TAC CTA TTG CCT ACG GCA GCC
TTCGAACGTA CGTTTAAGAT AAAGTTCCTC TGTCAGTATT TAC TTT ATG GAT AAC GGA TGC CGT CGG
68             SfiI                           PstI
ALA GLY LEU LEU LEU LEU ALA ALA GLN PRO ALA MET ALA GLU VAL GLN LEU GLN *** ***
GCT GGA TTG TTA TTA CTC GCG GCC CAG CCG GCC ATG GCC GAG GTG CAA CTG CAG TAA TAG
CGA CCT AAC AAT AAT GAG CGC CGG GTC GGC CGG TAC CGG CTC CAC GTT GAC GTC ATT ATC
128 NotI
ALA ALA ALA GLY GLY GLY GLY SER MET GLU SER ALA LYS GLU THR ARG TYR CYS ALA VAL
GCG GCC GCA GGG GGA GGA GGG TCC ATG GAA TCT GCC AAG GAG ACT CGC TAC TGT GCA GTG
CGC CGG CGT CCC CCT CCT CCC AGG TAC CTT AGA CGG TTC CTC TGA GCG ATG ACA CGT CAC
188
CYS ASN ASP TYR ALA SER GLY TYR HIS TYR GLY VAL TRP SER CYS GLU GLY CYS LYS ALA
TGC AAT GAC TAT GCT TCA GGC TAC CAT TAT GGA GTC TGG TCC TGT GAG GGC TGC AAG GCC
ACG TTA CTG ATA CGA AGT CCG ATG GTA ATA CCT CAG ACC AGG ACA CTC CCG ACG TTC CGG
248
PHE PHE LYS ARG SER ILE GLN GLY HIS ASN ASP TYR MET CYS PRO ALA THR ASN GLN CYS
TTC TTC AAG AGA AGT ATT CAA GGA CAT AAC GAC TAT ATG TGT CCA GCC ACC AAC CAG TGC
AAG AAG TTC TCT TCA TAA GTT CCT GTA TTG CTG ATA TAC ACA GGT CGG TGG TTG GTC ACG
308
THR ILE ASP LYS ASN ARG ARG LYS SER CYS GLN ALA CYS ARG LEU ARG LYS CYS TYR GLU
ACC ATT GAT AAA AAC AGG AGG AAG AGC TGC CAG GCC TGC CGG CTC CGT AAA TGC TAC GAA
TGG TAA CTA TTT TTG TCC TCC TTC TCG ACG GTC CGG ACG GCC GAG GCA TTT ACG ATG CTT
368
VAL GLY MET MET LYS GLY GLY ILE ARG LYS ASP ARG ARG GLY GLY ARG MET LEU LYS HIS
GTG GGA ATG ATG AAA GGT GGG ATA CGA AAA GAC CGA AGA GGA GGG AGA ATG TTG AAA CAC
CAC CCT TAC TAC TTT CCA CCC TAT GCT TTT CTG GCT TCT CCT CCC TCT TAC AAC TTT GTG
428
LYS ARG GLN ARG ASP ASP GLY GLU GLY ARG GLY GLU VAL GLY SER Ter Ter      HRE 1
AAG CGC CAG AGA GAT GAT GGG GAG GGC AGG GGT GAA GTG GGG TCT TGA TAA TCAGGTCAGAGT
TTC GCG GTC TCT CTA CTA CCC CTC CCG TCC CCA CTT CAC CCC AGA ACT ATT AGTCCAGTCTCA
491         HRE 1        SalI          HRE 2                       EcoRI
           GACCTGAGCTAAAATAACACATTCAG GTCGAC TTGGGTCAGTCTGACCGGGACAAAGTTAATGTAACCTC GAATTC
           CTGGACTCGATTTTATTGTGTAAGTC CAGCTG AACCCAGTCAGACTGGCCCTGTTTCAATTACATTGGAG CTTAAG
```

Figure 5

1 *Hin*DIII pelB
MET LYS TYR LEU LEU PRO THR ALA ALA
AAGCTTGCAT GCAAATTCTA TTTCAAGGAG ACAGTCATAA ATG AAA TAC CTA TTG CCT ACG GCA GCC
TTCGAACGTA CGTTTAAGAT AAAGTTCCTC TGTCAGTATT TAC TTT ATG GAT AAC GGA TGC CGT CGG 68
ALA GLY LEU LEU LEU LEU ALA ALA GLN PRO ALA MET ALA GLU MET GLU SER ALA LYS GLU
GCT GGA TTG TTA TTA CTC GCG GCC CAG CCG GCA ATG GCC GAG ATG GAA TCT GCC AAG GAG
CGA CCT AAC AAT AAT GAG CGC CGG GTC GGC CGT TAC CGG CTC TAC CTT AGA CGG TTC CTC 128
THR ARG TYR CYS ALA VAL CYS ASN ASP TYR ALA SER GLY TYR HIS TYR GLY VAL TRP SER
ACT CGC TAC TGT GCA GTG TGC AAT GAC TAT GCT TCA GGC TAC CAT TAT GGA GTC TGG TCC
TGA GCG ATG ACA CGT CAC ACG TTA CTG ATA CGA AGT CCG ATG GTA ATA CCT CAG ACC AGG 188
CYS GLU GLY CYS LYS ALA PHE PHE LYS ARG SER ILE GLN GLY HIS ASN ASP TYR MET CYS
TGT GAG GGC TGC AAG GCC TTC TTC AAG AGA AGT ATT CAA GGA CAT AAC GAC TAT ATG TGT
ACA CTC CCG ACG TTC CGG AAG AAG TTC TCT TCA TAA GTT CCT GTA TTG CTG ATA TAC ACA 248
PRO ALA THR ASN GLN CYS THR ILE ASP LYS ASN ARG ARG LYS SER CYS GLN ALA CYS ARG
CCA GCC ACC AAC CAG TGC ACC ATT GAT AAA AAC AGG AGG AAG AGC TGC CAG GCC TGC CGG
GGT CGG TGG TTG GTC ACG TGG TAA CTA TTT TTG TCC TCC TTC TCG ACG GTC CGG ACG GCC 308
LEU ARG LYS CYS TYR GLU VAL GLY MET MET LYS GLY GLY ILE ARG LYS ASP ARG ARG GLY
CTC CGT AAA TGC TAC GAA GTG GGA ATG ATG AAA GGT GGG ATA CGA AAA GAC CGA AGA GGA
GAG GCA TTT ACG ATG CTT CAC CCT TAC TAC TTT CCA CCC TAT GCT TTT CTG GCT TCT CCT 368
GLY ARG MET LEU LYS HIS LYS ARG GLN ARG ASP ASP GLY GLU GLY ARG GLY GLU VAL GLY
GGG AGA ATG TTG AAA CAC AAG CGC CAG AGA GAT GAT GGG GAG GGC AGG GGT GAA GTG GGG
CCC TCT TAC AAC TTT GTG TTC GCG GTC TCT CTA CTA CCC CTC CCG TCC CCA CTT CAC CCC 428
*Sfi* I        *Pst* I      *Not* I
SER GLY GLY GLY GLY SER ALA GLN PRO ALA LEU LEU GLN LEU ALA ALA ALA TER
TCT GGG GGA GGA GGG TCG GCC CAG CCG GCC CTC CTG CAG CTG GCG GCC GCA TAACTGATTG
AGA CCC CCT CCT CCC AGC CGG GTC GGC CGG GAG GAC GTC GAC CGC CGG CGT ATTGACTAAC 489 *Sal* I                                          Eco RI
AGTCGAC TTG GGTCAGTCTG ACCGGGACAA AGTTAATGTA ACCTC GAATTC
TCAGCTG AAC CCAGTCAGAC TGGCCCTGTT TCAATTACAT TGGAG CTTAAG
                          HRE

HEAVY CHAIN

Figure 9

```
Q   V   Q   L   Q   Q   S   G   G   G   V   V   Q   P   G   R   S   L
CAGGTACAGCTGCAGCAGTCAGGGGGAGGCGTGGTCCAGCCTGGGAGGTCCCTG
GTCCATGTCGACGTCGTCAGTCCCCCTCCGCACCAGGTCGGACCCTCCAGGGAC

R   L   S   C   A   A   S   G   F   P   F   S   T   Y   G   M   H   W
AGACTCTCCTGTGCAGCCTCGGGATTCCCCTTTAGTACTTATGGCATGCACTGG
TCTGAGAGGACACGTCGGAGCCCTAAGGGGAAATCATGAATACCGTACGTGACC

R   Q   A   V   P   G   K   G   L   E   W   V   A   V   I   S   Y   D
CGCCAGGCTGTCCCAGGCAAGGGGCTGGAGTGGGTGGCAGTTATATCATATGAT
GCGGTCCGACAGGGTCCGTTCCCCGACCTCACCCACCGTCAATATAGTATACTA

G   S   N   K   Y   Y   A   D   S   V   K   G   R   F   T   I   S   R
GGAAGTAATAAATACTACGCAGACTCCGTGAAGGGCCGATTCACCATCTCCAGA
CCTTCATTATTTATGATGCGTCTGAGGCACTTCCCGGCTAAGTGGTAGAGGTCT

D   N   S   K   N   T   L   Y   L   Q   M   N   S   L   R   A   E   D
GACAATTCCAAGAACACGTTGTATCTGCAAATGAACAGCCTGAGAGCTGAGGAC
CTGTTAAGGTTCTTGTGCAACATAGACGTTTACTTGTCGGACTCTCGACTCCTG

T   A   V   Y   Y   C   A   R   D   L   D   P   T   R   Y   S   S   G
ACGGCTGTGTATTACTGTGCGAGAGATTTAGACCCCACCAGGTATAGCAGTGGC
TGCCGACACATAATGACACGCTCTCTAAATCTGGGGTGGTCCATATCGTCACCG

W   D   T   D   Y   W   G   Q   G   H   L   V   T   V   S   S
TGGGACACTGACTACTGGGGCCAGGGGCACCTGGTCACTGTCTCCTCA
ACCCTGTGACTGATGACCCCGGTCCCCGTGGACCAGTGACAGAGGAGT
```

LIGHT CHAIN

```
E   T   T   L   T   Q   S   P   G   T   L   S   L   S   P   G   E   R
GAAACGACACTCACGCAGTCTCCAGGCACCCTGTCTTTGTCTCCGGGGGAAAGA
CTTTGCTGTGAGTGCGTCAGAGGTCCGTGGGACAGAAACAGAGGCCCCCTTTCT

A   T   L   S   C   R   A   S   Q   N   I   G   S   S   S   L   A   W
GCCACCCTCTCCTGCAGGGCCAGTCAGAATATTGGCAGCAGCTCCTTAGCCTGG
CGGTGGGAGAGGACGTCCCGGTCAGTCTTATAACCGTCGTCGAGGAATCGGACC

Y   Q   Q   K   P   G   Q   A   P   R   L   L   I   Y   G   A   S   T
TACCAACAGAAACCTGGCCAGGCTCCCAGGCTCCTCATCTATGGTGCATCCACC
ATGGTTGTCTTTGGACCGGTCCGAGGGTCCGAGGAGTAGATACCACGTAGGTGG

R   A   T   G   F   S   G   S   G   S   G   T   Q   F   T   L   T   I
AGGGCCACTGGTTTCAGTGGCAGTGGGTCAGGGACACAATTCACTCTCACCATC
TCCCGGTGACCAAAGTCACCGTCACCCAGTCCCTGTGTTAAGTGAGAGTGGTAG

I   P   A   R   S   S   L   Q   S   E   D   F   A   V   Y   Y   C   Q
ATCCCAGCCAGGAGCAGCCTGCAGTCTGAAGATTTTGCAGTTTATTACTGTCAG
TAGGGTCGGTCCTCGTCGGACGTCAGACTTCTAAAACGTCAAATAATGACAGTC

Q   Y   N   F   W   P   F   T   F   G   P   G   T   K   L   E   I   K
CAGTATAATTTCTGGCCATTCACTTTTGGCCCTGGGACCAAGCTGGAGATCAAA
GTCATATTAAAGACCGGTAAGTGAAAACCGGGACCCTGGTTCGACCTCTAGTTT

R
CGT
GCA
```

CHIMERIC BINDING PEPTIDE LIBRARY SCREENING METHOD

The present invention relates generally to methods for screening nucleotide libraries for sequences that encode peptides of interest.

Isolating an unknown gene which encodes a desired peptide from a recombinant DNA library can be a difficult task. The use of hybridisation probes may facilitate the process, but their use is generally dependent on knowing at least a portion of the sequence of the gene which encodes the protein. When the sequence is not known, DNA libraries can be expressed in an expression vector, and antibodies have been used to screen for plaques or colonies displaying the desired protein antigen. This procedure has been useful in screening small libraries, but rarely occurring sequences which are represented in less than about 1 in $10^5$ clones (as is the case with rarely occurring cDNA molecules or synthetic peptides) can be easily missed, making screening libraries larger than $10^6$ clones at best laborious and difficult. Methods designed to address the isolation of rarely occurring sequences by screening libraries of $10^6$ clones have been developed and include phage display methods and LacI fusion phage display, discussed in more detail below.

Phage display methods. Members of DNA libraries which are fused to the N-terminal end of filamentous bacteriophage pIII and pVIII coat proteins have been expressed from an expression vector resulting in the display of foreign peptides on the surface of the phage particle with the DNA encoding the fusion protein packaged in the phage particle (Smith G. P., 1985, Science 228: 1315-1317). The expression vector can be the bacteriophage genome itself, or a phagemid vector, into which a bacteriophage coat protein has been cloned. In the latter case, the host bacterium, containing the phagemid vector, must be co-infected with autonomously replicating bacteriophage, termed helper phage, to provide the full complement of proteins necessary to produce mature phage particles. The helper phage normally has a genetic defect in the origin of replication which results in the preferential packaging of the phagemid genome. Expression of the fusion protein following helper phage infection, allows incorporation of both fusion protein and wild type coat protein into the phage particle during assembly. Libraries of fusion proteins incorporated into phage, can then be selected for binding members against targets of interest (ligands). Bound phage can then be allowed to reinfect Escherichia coli (E. coli) bacteria and then amplified and the selection repeated, resulting in the enrichment of binding members (Parmley, S. F., & Smith, G. P. 1988., Gene 73: 305-318; Barrett R. W. et al., 1992, Analytical Biochemistry 204: 357-364 Williamson et al., Proc. Natl. Acad. Sci. USA, 90: 4141-4145; Marks et al., 1991, J. Mol. Biol. 222: 581-597).

Several publications describe this method. For example, U.S. Pat. No. 5,403,484 describes production of a chimeric protein formed from the viral coat protein and the peptide of interest. In this method at least a functional portion of a viral coat protein is required to cause display of the chimeric protein or a processed form thereof on the outer surface of the virus. In addition, U.S. Pat. No. 5,571,698 describes a method for obtaining a nucleic acid encoding a binding protein, a key component of which comprises preparing a population of amplifiable genetic packages which have a genetically determined outer surface protein, to cause the display of the potential binding domain on the outer surface of the genetic package. The genetic packages are selected from the group consisting of cells, spores and viruses. For example when the genetic package is a bacterial cell, the outer surface transport signal is derived from a bacterial outer surface protein, and when the genetic package is a filamentous bacteriophage, the outer surface transport signal is provided by the gene pIII (minor coat protein) or pVIII (major coat protein) of the filamentous phage.

WO-A-92/01047 and WO-A-92/20791 describe methods for producing multimeric specific binding pairs, by expressing a first polypeptide chain fused to a viral coat protein, such as the gene pIII protein, of a secreted replicable genetic display package (RGDP) which displays a polypeptide at the surface of the package, and expressing a second polypeptide chain of the multimer, and allowing the two chains to come together as part of the RGDP.

LacI fusion plasmid display. This method is based on the DNA binding ability of the lac repressor. Libraries of random peptides are fused to the lacI repressor protein, normally to the C-terminal end, through expression from a plasmid vector carrying the fusion gene. Linkage of the LacI-peptide fusion to its encoding DNA occurs via the lacO sequences-on the plasmid, forming a stable peptide-LacI-peptide complex. These complexes are released from their host bacteria by cell lysis, and peptides of interest isolated by affinity purification on an immobilised target. The plasmids thus isolated can then be reintroduced into E. coli by electroporation to amplify the selected population for additional rounds of screening (Cull, M. G. et al. 1992. Proc. Natl. Acad. Sci. U.S.A. 89:1865-1869).

U.S. Pat. No. 5,498,530 describes a method for constructing a library of random peptides fused to a DNA binding protein in appropriate host cells and culturing the host cells under conditions suitable for expression of the fusion proteins intra-cellularly, in the cytoplasm of the host cells. This method also teaches that the random peptide is located at the carboxy terminus of the fusion protein and that the fusion protein-DNA complex is released from the host cell by cell lysis. No method is described for the protection of the DNA from degradation once released from the lysed cell. Several DNA binding proteins are claimed but no examples are shown except lacI.

There remains a need for methods of constructing peptide libraries in addition to the methods described above. For instance, the above methods do not permit production of secreted peptides with a free carboxy terminus. The present invention describes an alternative method for isolating peptides of interest from libraries and has significant advantages over the prior art methods.

In general terms, the present invention provides a method for screening a nucleotide library (usually a DNA library) for a nucleotide sequence which encodes a target peptide of interest. The method involves physically linking each peptide to a polynucleotide including the specific nucleotide sequence encoding that peptide. Linkage of a peptide to its encoding nucleotide sequence is achieved via linkage of the peptide to a nucleotide binding domain. A bifunctional chimeric protein with a nucleotide binding domain and a library member or target peptide (preferably with a function of interest) is thus obtained. The peptide of interest is bound to the polynucleotide encoding that peptide via the nucleotide binding domain of the chimeric protein.

The polynucleotide-chimeric protein complex is then incorporated within a peptide display carrier package (PDCP), protecting the polynucleotide from subsequent degradation, while displaying the target peptide portion on the outer surface of the peptide display carrier package (PDCP).

Thus, in one aspect, the present invention provides a peptide display carrier package (PDCP), said package comprising a polynucleotide-chimeric protein complex wherein the chimeric protein has a nucleotide binding portion and a target peptide portion, wherein said polynucleotide comprises a nucleotide sequence motif which is specifically bound by said nucleotide binding portion, and wherein at least the chimeric protein encoding portion of the polynucleotide not bound by the nucleotide binding portion of the chimeric protein is protected.

In one embodiment the polynucleotide is protected by a protein which binds non-specifically to naked polynucleotide. Examples include viral coat proteins, many of which are well-known in the art. Where the chosen viral coat protein requires an initiation sequence to commence general binding to the polynucleotide, this will be provided on the polynucleotide at appropriate location(s). A preferred coat protein is coat protein from a bacteriophage, especially M13.

Generally, the nucleic binding portion of the chimeric protein is selected for its specificity for the nucleotide sequence motif present in the recombinant polynucleotide encoding the chimeric protein.

Optionally, the nucleotide sequence motif may be an integral part of the protein encoding region of the polynucleotide. Alternatively, and more usually, the motif may be present in a non-coding region of the polynucleotide. For the purposes of this invention, all that is required is for the motif to be located on the polynucleotide such that the nucleotide binding portion of the chimeric protein is able to recognise and bind to it. Desirably the polynucleotide-chimeric protein complex has a dissociation constant of at least one hour.

Optionally, the recombinant polynucleotide may comprise two or more nucleotide sequence motifs, each of which will be bound by a chimeric protein molecule. Preferably, the motifs are positioned along the length of the polynucleotide to avoid steric hindrance between the bound chimeric proteins.

Preferably, the nucleotide sequence motif is not affected by the presence of additional nucleotide sequence (e.g., encoding sequence) at its 5' and/or 3' ends. Thus the chimeric fusion protein may include a target peptide portion at its N terminal end, at its C terminal end or may include two target peptide portions (which may be the same or different) at each end of the nucleotide binding portion, ie at both the N and C terminal ends of the chimeric protein. For example one target peptide may be an antibody of known specificity and the other peptide may be a peptide of potential interest.

Desirably the target peptide portion of the chimeric protein is displayed externally on the peptide display carrier package, and is thus available for detection, reaction and/or binding.

In more detail the PDCP may be composed two distinct elements:
a. A polynucleotide-chimeric protein complex. This links the displayed target peptide portion to the polynucleotide encoding that peptide portion through a specific polynucleotide binding portion. The nucleotide sequence encoding the chimeric protein, and the specific nucleotide sequence motif recognised by the nucleotide binding portion of the chimeric protein must be present on a segment of polynucleotide which can be incorporated into the PDCP; and
b. A protective coat. This may be supplied by a replicable carrier or helper package capable of independent existence. Alternatively, a coat protein could be encoded by the recombinant polynucleotide of the invention. The protective coat for the polynucleotide-chimeric protein complex may be composed of a biological material such as protein or lipid, but the protective coat is not required for linking the target peptide to the polynucleotide encoding that peptide. The protective coat must allow the display of the target peptide portion of the chimeric protein on its outer surface. The carrier or helper package may also provide the mechanism for releasing the intact PDCP from host cells when so required. By way of example, when a bacteriophage is the replicable carrier package, a protein coat of the bacteriophage surrounds the polynucleotide-chimeric protein complex to form the PDCP, which is then extruded from the host bacterial cell.

The invention described herein demonstrates that peptides fused to a nucleotide binding domain can be displayed externally, even through a bacteriophage carrier package protein coat, while still bound to the polynucleotide encoding the displayed peptide.

The present invention also provides a recombinant polynucleotide comprising a nucleotide sequence encoding a chimeric protein having a nucleotide binding portion operably linked to a target peptide portion, wherein said polynucleotide includes a specific nucleotide sequence motif which is bound by the nucleotide binding portion of said chimeric protein and further encoding a non-sequence-specific nucleotide binding protein.

Desirably, the recombinant polynucleotide is a recombinant expression system, able to express the chimeric protein when placed in a suitable environment, for example a compatible host cell. After its expression, the chimeric protein binds to the specific nucleotide sequence (motif) present in the polynucleotide comprising the nucleotide sequence encoding the chimeric protein.

Optionally there may be a linker sequence located between the nucleotide sequence encoding the nucleotide binding portion and the polynucleotide inserted into the restriction enzyme site of the construct.

Desirably the nucleotide binding portion is a DNA binding domain of an oestrogen or progesterone receptor, or a functional equivalent thereof. Examples of sequences encoding such nucleotide binding portions are set out in SEQ ID Nos 11 and 13.

The term "expression system" is used herein to refer to a genetic sequence which includes a protein-encoding region and is operably linked to all of the genetic signals necessary to achieve expression of that region. Optionally, the expression system may also include regulatory elements, such as a promoter or enhancer to increase transcription and/or translation of the protein encoding region or to provide control over expression. The regulatory elements may be located upstream or downstream of the protein encoding region or within the protein encoding region itself. Where two or more distinct protein encoding regions are present these may use common regulatory element(s) or have separate regulatory element(s).

Generally, the recombinant polynucleotide described above will be DNA. Where the expression system is based upon an M13 vector, usually the polynucleotide binding portion of the expressed chimeric portion will be single-stranded DNA. However, other vector systems may be used and the nucleotide binding portion may be selected to bind preferentially to double-stranded DNA or to double or single-stranded RNA, as convenient.

Additionally the present invention provides a vector containing such a recombinant expression system and host cells transformed with such a recombinant expression system (optionally in the form of a vector).

Whilst the recombinant polynucleotide described above forms an important part of the present invention, we are also concerned with the ability to screen large (e.g. of at least $10^5$ members, for example $10^6$ or even $10^7$ members) libraries of genetic material. One of the prime considerations therefore is the provision of a recombinant genetic construct into which each member of said library can individually be incorporated to form the recombinant polynucleotide described above and to express the chimeric protein thereby encoded (the target peptide of which is encoded by the nucleotide library member incorporated into the construct).

Thus viewed in a further aspect the present invention provides a genetic construct or set of genetic constructs comprising a polynucleotide having a sequence which includes:

i) a sequence encoding a nucleotide binding portion able to recognise and bind to a specific sequence motif;
ii) the sequence motif recognised and bound by the nucleotide binding portion encoded by (i);
iii) a restriction enzyme site which permits insertion of a polynucleotide, said site being designed to operably link said polynucleotide to the sequence encoding the nucleotide binding portion so that expression of the operably linked polynucleotide sequences yields a chimeric protein; and
iv) a sequence encoding a nucleotide binding protein which binds non-specifically to naked polynucleotide.

Optionally there may be a linker sequence located between the nucleotide sequence encoding the nucleotide binding portion and the sequence of the polynucleotide from the library inserted into the restriction enzyme site of the construct.

Desirably the nucleotide binding portion is a DNA binding domain of an oestrogen or progesterone receptor, or a functional equivalent thereof. Examples of sequences encoding such nucleotide binding portions are set out in SEQ ID Nos 11 and 13.

Suitable genetic constructs according to the invention include pDM12, pDM14 and pDM16, deposited at NCIMB on 28 Aug. 1998 under Nos NCIMB 40970, NCIMB 40971 and NCIMB 40972 respectively.

It is envisaged that a conventionally produced genetic library may be exposed to the genetic construct(s) described above. Thus, each individual member of the genetic library will be separately incorporated into the genetic construct and the library will be present in the form of a library of recombinant polynucleotides (as described above), usually in the form of vectors, each recombinant polynucleotide including as library member.

Thus, in a further aspect, the present invention provides a library of recombinant polynucleotides (as defined above) wherein each polynucleotide includes a polynucleotide obtained from a genetic library and which encodes the target peptide portion of the chimeric protein expressed by the recombinant polynucleotide.

Optionally, the chimeric protein may further include a linker sequence located between the nucleotide binding portion and the target peptide portion. The linker sequence will reduce steric interference between the two portions of the protein. Desirably the linker sequence exhibits a degree of flexibility.

Also disclosed are methods for constructing and screening libraries of PDCP particles, displaying many different peptides, allowing the isolation and identification of particular peptides by means of affinity techniques relying on the binding activity of the peptide of interest. The resulting polynucleotide sequences can therefore be more readily identified, re-cloned and expressed.

A method of constructing a genetic library, said method comprising:
a) constructing multiple copies of a recombinant vector comprising a polynucleotide sequence which encodes a nucleotide binding portion able to recognise and bind to a specific sequence motif (and optionally also including the specific sequence motif);
b) operably linking each said vector to a polynucleotide encoding a target polypeptide, such that expression of said operably linked vector results in expression of a chimeric protein comprising said target peptide and said nucleotide binding portions; wherein said multiple copies of said operably linked vectors collectively express a library of target peptide portions;
c) transforming host cells with the vectors of step b);
d) culturing the host cells of step c) under conditions suitable for expression of said chimeric protein;
e) providing a recombinant polynucleotide comprising the nucleotide sequence motif specifically recognised by the nucleotide binding portion and exposing this polynucleotide to the chimeric protein of step d) to yield a polynucleotide-chimeric protein complex; and
f) causing production of a non-sequence-specific moiety able to bind to the non-protected portion of the polynucleotide encoding the chimeric protein to form a peptide display carrier package.

The present invention further provides a method of screening a genetic library, said method comprising:
a) exposing the polynucleotide members of said library to multiple copies of a genetic construct comprising a nucleotide sequence encoding a nucleotide binding portion able to recognise and bind to a specific sequence motif, under conditions suitable for the polynucleotides of said library each to be individually ligated into one copy of said genetic construct, to create a library of recombinant polynucleotides;
b) exposing said recombinant polynucleotides to a population of host cells, under conditions suitable for transformation of said host cells by said recombinant polynucleotides;
c) selecting for transformed host cells;
d) exposing said transformed host cells to conditions suitable for expression of said recombinant polynucleotide to yield a chimeric protein; and
e) providing a recombinant polynucleotide comprising the nucleotide sequence motif specifically recognised by the nucleotide binding portion and exposing this polynucleotide to the chimeric protein of step d) to yield a polynucleotide-chimeric protein complex;
f) protecting any exposed portions of the polynucleotide in the complex of step e) to form a peptide display carrier package; and
g) screening said peptide display carrier package to select only those packages displaying a target peptide portion having the characteristics required.

Desirably in step a) the genetic construct is pDM12, pDM14 or pDM16.

Desirably in step f) the peptide display package carrier is extruded from the transformed host cell without lysis of the host cell.

Generally the transformed host cells will be plated out or otherwise divided into single colonies following transformation and prior to expression of the chimeric protein.

The screening step g) described above may look for a particular target peptide either on the basis of function (e.g. enzymic activity) or structure (e.g. binding to a specific antibody). Once the peptide display carrier package is observed to include a target peptide with the desired characteristics, the polynucleotide portion thereof (which of course encodes the chimeric protein itself) can be amplified, cloned and otherwise manipulated using standard genetic engineering techniques.

The current invention differs from the prior art teaching of the previous disclosures U.S. Pat. Nos. 5,403,484 and 5,571,698, as the invention does not require outer surface transport signals, or functional portions of viral coat proteins, to enable the display of chimeric binding proteins on the outer surface of the viral particle or genetic package.

The current invention also differs from the teaching of WO-A-92/01047 and WO-A-92/20791, as no component of a secreted replicable genetic display package, or viral coat protein is required, to enable display of the target peptide on the outer surface of the viral particle.

The current invention differs from the teaching of U.S. Pat. No. 5,498,530, as it enables the display of chimeric proteins, linked to the polynucleotide encoding the chimeric protein, extra-cellularly, not in the cytoplasm of a host cell. In the current invention the chimeric proteins are presented on the outer surface of a peptide display carrier package (PDCP) which protects the DNA encoding the chimeric protein, and does not require cell lysis to obtain access to the chimeric protein-DNA complex. Finally, the current invention does not rely upon the lacI DNA binding protein to form the chimeric protein-DNA complex.

In one embodiment of the invention, the nucleotide binding portion of the chimeric protein comprises a DNA binding domain from one or more of the nuclear steroid receptor family of proteins, or a functional equivalent of such a domain. Particular examples include (but are not limited to) a DNA binding domain of the oestrogen receptor or the progesterone receptor, or functional equivalents thereof. These domains can recognise specific DNA sequences, termed hormone response elements (HRE), which can be bound as both double and single-stranded DNA. The DNA binding domain of such nuclear steroid receptor proteins is preferred.

The oestrogen receptor is especially referred to below by way of example, for convenience since:
(a) The oestrogen receptor is a large multifunctional polypeptide of 595 amino acids which functions in the cytoplasm and nucleus of eukaryotic cells (Green et al., 1986, Science 231: 1150-1154). A minimal high affinity DNA binding domain (DBD) has been defined between amino acids 176 and 282 (Mader et al., 1993, Nucleic Acids Res. 21: 1125-1132). The functioning of this domain (i.e. DNA binding) is not inhibited by the presence of non-DNA binding domains at both the N and C terminal ends of this domain, in the full length protein.
(b) The oestrogen receptor DNA binding domain fragment (amino acids 176-282) has been expressed in *E. coli* and shown to bind to the specific double stranded-DNA oestrogen receptor target HRE nucleotide sequence, as a dimer with a similar affinity (0.5 nM) to the parent molecule (Murdoch et al. 1990, Biochemistry 29: 8377-8385; Mader et al., 1993, Nucleic Acids Research 21: 1125-1132). DBD dimerization on the surface of the PDCP should result in two peptides displayed per particle. This bivalent display can aid in the isolation of low affinity peptides and peptides that are required to form a bivalent conformation in order to bind to a particular target, or activate a target receptor. The oestrogen receptor is capable of binding to its 38 base pair target HRE sequence, consensus sequence:

SEQ ID No 77
1)  5'-TCAGGTCAGAGTGACCTGAGCTAAAATAACACATTCAG-3'
    ("minus strand"),
and SEQ ID No 78
2)  3'-AGTCCAGTCTCACTGGACTCGATTTTATTGTGTAAGTC-5'
    ("plus strand"), with high affinity and specificity, under the salt and pH conditions normally required for selection of binding peptides. Moreover, binding affinity is increased 60-fold for the single-stranded coding, or "plus", strand (i.e. SEQ ID No 78) of the HRE nucleotide sequence over the double stranded form of the specific target nucleotide sequence (Peale et al. 1988, Proc. Natl. Acad. Sci. USA 85: 1038-1042; Lannigan & Notides, 1989, Proc. Natl. Acad. Sci. USA 86: 863-867).

In an embodiment of the invention where the DNA binding component of the peptide display carrier package is the oestrogen receptor, the nucleotide (DNA) binding portion-contains a minimum sequence of amino acids 176-282 of the oestrogen receptor protein. In addition, the consensus oestrogen receptor target HRE sequence is cloned in such a way that if single stranded DNA can be produced-then the coding, or "plus", strand of the oestrogen receptor HRE nucleotide sequence is incorporated into single-stranded DNA. An example of a vector suitable for this purpose is pUC119 (see Viera et al., Methods in Enzymology, Vol 153, pages 3-11, 1987).

In a preferred embodiment of the invention a peptide display carrier package (PDCP) can be assembled when a bacterial host cell is transformed with a bacteriophage vector, which vector comprises a recombinant polynucleotide as described above. The expression vector will also comprise the specific nucleotide motif that can be bound by the nucleotide binding portion of the chimeric protein. Expression of recombinant polynucleotide results in the production of the chimeric protein which comprises the target peptide and the nucleotide binding portion. The host cell is grown under conditions suitable for chimeric protein expression and assembly of the bacteriophage particles, and the association of the chimeric protein with the specific nucleotide sequence in the expression vector. In this embodiment, since the vector is a bacteriophage, which replicates to produce a single-stranded DNA, the nucleotide binding portion preferably has an affinity for single-stranded DNA. Incorporation of the vector single-stranded DNA-chimeric protein complex into bacteriophage particles results in the assembly of the peptide display carrier package (PDCP), and display of the target peptide on the outer surface of the PDCP.

In this embodiment both of the required elements for producing peptide display carrier packages are contained on the same vector. Incorporation of the DNA-chimeric protein complex into a peptide display carrier package (PDCP) is preferred as DNA degradation is prevented, large numbers of PDCPs are produced per host cell, and the PDCPs are easily separated from the host cell without recourse to cell lysis.

In a more preferred embodiment, the vector of the is a phagemid vector (for example pUC119) where expression of the chimeric protein is controlled by an inducible promoter. In this embodiment the PDCP can only be assembled following infection of the host cell with both phagemid vector and helper phage. The transfected host cell is then cultivated under conditions suitable for chimeric protein expression and assembly of the bacteriophage particles.

In this embodiment the elements of the PDCP are provided by two separate vectors. The phagemid derived PDCP is superior to phagemid derived display packages disclosed in WO-A-92/01047 where a proportion of packages displaying bacteriophage coat protein fusion proteins will contain the helper phage DNA, not the fusion protein DNA sequence. In the current invention, a PDCP can display the chimeric fusion protein only when the package contains the specific nucleotide motif recognised by the nucleotide binding portion. In most embodiments this sequence will be present on the same DNA segment that encodes the fusion protein. In addition, the prior art acknowledges that when mutant and wild type proteins are co-expressed in the same bacterial cell, the wild type protein is produced preferentially. Thus, when the wild type helper phage, phage display system of WO-A-92/01047 is used, both wild type gene pIII and target peptide-gene pIII chimeric proteins are produced in the same cell. The result of this is that the wild type gene pIII protein is preferentially packaged into bacteriophage particles, over the chimeric protein. In the current invention, there is no competition with wild type bacteriophage coat proteins for packaging.

Desirably the target peptide is displayed in a location exposed to the external environment of the PDCP, after the PDCP particle has been released from the host cell without recourse to cell lysis. The target peptide is then accessible for binding to its ligand. Thus, the target peptide may be located at or near the N-terminus or the C-terminus of a nucleotide binding domain, for example the DNA binding domain of the oestrogen receptor.

The present invention also provides a method for screening a DNA library expressing one or more polypeptide chains that are processed, folded and assembled in the periplasmic space to achieve biological activity. The PDCP may be assembled by the following steps:

(a) Construction of N- or C-terminal DBD chimeric protein fusions in a phagemid vector.
  (i) When the target peptide is located at the N-terminus of the nucleotide binding portion, a library of DNA sequences each encoding a potential target peptide is cloned into an appropriate location of an expression vector (i.e. behind an appropriate promoter and translation sequences and a sequence encoding a signal peptide leader directing transport of the downstream fusion protein to the periplasmic space) and upstream of the sequence encoding the nucleotide binding portion. In a preferred embodiment the DNA sequence(s) of interest may be joined, by a region of DNA encoding a flexible amino acid linker, to the 5'-end of an oestrogen receptor DBD.
  (ii) Alternatively, when the target peptide is located at the C-terminus of the nucleotide binding domain, a library of DNA sequences each encoding a potential target peptide is cloned into the expression vector so that the nucleotide sequence coding for the nucleotide binding portion is upstream of the cloned DNA target peptide encoding sequences, said nucleotide binding portion being positioned behind an appropriate promoter and translation sequences and a sequence encoding a signal peptide leader directing transport of the downstream fusion protein to the periplasmic space. In a preferred embodiment, DNA sequence(s) of interest may be joined, by a region of DNA encoding a flexible amino acid linker oestrogen receptor DBD DNA sequence.

Located on the expression vector is the specific HRE nucleotide sequence recognised, and bound, by the oestrogen receptor DBD. In order to vary the number of chimeric proteins displayed on each PDCP particle, this sequence can be present as one or more copies in the vector.

(b) Incorporation into the PDCP. Non-lytic helper bacteriophage infects host cells containing the expression vector. Preferred types of bacteriophage include the filamentous phage fd, f1 and M13. In a more preferred embodiment the bacteriophage may be M13K07.

The protein(s) of interest are expressed and transported to the periplasmic space, and the properly assembled proteins are incorporated into the PDCP particle by virtue of the high affinity interaction of the DBD with the specific target nucleotide sequence present on the phagemid vector DNA which is naturally packaged into phage particles in a single-stranded form. The high affinity interaction between the DBD protein and its specific target nucleotide sequence prevents displacement by bacteriophage coat proteins resulting in the incorporation of the protein(s) of interest onto the surface of the PDCP as it is extruded from the cell.

(c) Selection of the peptide of interest. Particles which display the peptide of interest are then selected from the culture by affinity enrichment techniques.

This is accomplished by means of a ligand specific for the protein of interest, such as an antigen if the protein of interest is an antibody. The ligand may be presented on a solid surface such as the surface of an ELISA plate, or in solution. Repeating the affinity selection procedure provides an enrichment of clones encoding the desired sequences, which may then be isolated for sequencing, further cloning and/or expression.

Numerous types of libraries of peptides fused to the DBD can be screened under this embodiment including:
  (i) Random peptide sequences encoded by synthetic DNA of variable length.
  (ii) Single-chain Fv antibody fragments. These consist of the antibody heavy and light chain variable region domains joined by a flexible linker peptide to create a single-chain antigen binding molecule.
  (iii) Random fragments of naturally occurring proteins isolated from a cell population containing an activity of interest.

In another embodiment the invention concerns methods for screening a DNA library whose members require more than one chain for activity, as required by, for example, antibody Fab fragments for ligand binding. In this embodiment heavy or light chain antibody DNA is joined to a nucleotide sequence encoding a DNA binding domain of, for example, the oestrogen receptor in a phagemid vector. Typically the antibody DNA library sequences for either the heavy (VH and CH1) or light chain (VL and CL) genes are inserted in the 5' region of the oestrogen receptor DBD DNA, behind an appropriate promoter and translation sequences and a sequence encoding a signal peptide leader directing transport of the downstream fusion protein to the periplasmic space.

Thus, a DBD fused to a DNA library member-encoded protein is produced and assembled in to the viral particle after infection with bacteriophage. The second and any subsequent chain(s) are expressed separately either:
(a) from the same phagemid vector containing the DBD and the first polypeptide fusion protein, or
(b) from a separate region of DNA which may be present in the host cell nucleus, or on a plasmid, phagemid or bacteriophage expression vector that can co-exist, in the same host cell, with the first expression vector, so as to be transported to the periplasm where they assemble with the first chain that is fused to the DBD protein as it exits the cell. Peptide display carrier packages (PDCP) which encode the protein of interest can then be selected by means of a ligand specific for the protein.

In yet another embodiment, the invention concerns screening libraries of bi-functional peptide display carrier packages where two or more activities of interest are displayed on each PDCP. In this embodiment, a first DNA library sequence(s) is inserted next to a first DNA binding domain (DBD) DNA sequence, for example the oestrogen receptor DBD, in an appropriate vector, behind an appropriate promoter and translation sequences and a sequence encoding a signal peptide leader directing transport of this first chimeric protein to the periplasmic space. A second chimeric protein is also produced from the same, or separate, vector by inserting a second DNA library sequence(s) next to a second DBD DNA sequence which is different from the first DBD DNA sequence, for example the progesterone receptor DBD, behind an appropriate promoter and translation sequences and a sequence encoding a signal peptide leader. The first, or only, vector contains the specific HRE nucleotide sequences for both oestrogen and progesterone receptors. Expression of the two chimeric proteins, results in a PDCP with two different chimeric proteins displayed. As an example, one chimeric protein could possess a binding activity for a particular ligand of interest, while the second chimeric protein could possess an enzymatic activity. Binding by the PDCP to the ligand of the first chimeric protein could then be detected by subsequent incubation with an appropriate substrate for the second chimeric protein. In an alternative embodiment a bi-functional PDCP may be created using a single DBD, by cloning one peptide at the 5'-end of the DBD, and a second peptide at the 3'-end of the DBD. Expression of this single bi-functional chimeric protein results in a PDCP with two different activities.

We have investigated the possibility of screening libraries of peptides, fused to a DNA binding domain and displayed on the surface of a display package, for particular peptides with a biological activity of interest and recovering the DNA encoding that activity. Surprisingly, by manipulating the oestrogen receptor DNA binding domain in conjunction with M13 bacteriophage we have been able to construct novel particles which display large biologically functional molecules, that allows enrichment of particles with the desired specificity.

The invention described herein provides a significant breakthrough in DNA library screening technology.

The invention will now be further described by reference to the non-limiting examples and figures below.

DESCRIPTION OF FIGURES

FIG. 1 shows the pDM12 N-terminal fusion oestrogen receptor DNA binding domain expression vector nucleotide sequence (SEQ ID No 1), between the HindIII and EcoRI restriction sites, comprising a pelB leader secretion sequence (in italics) (SEQ ID No 2), multiple cloning site containing SfiI and NotI sites, flexible (glycine)$_4$-serine linker sequence (boxed), a fragment of the oestrogen receptor gene comprising amino acids 176-282 (SEQ ID No 3) of the full length molecule, and the 38 base pair consensus oestrogen receptor DNA binding domain HRE sequence.

FIG. 3 shows partial DNA (SEQ ID No 4) and amino acid (SEQ ID No 5) sequence for the human immunoglobulin kappa constant region (Kabat, E. A. et al., Sequences of Proteins of Immunological Interest. 4$^{th}$ edition. U.S. Department of Health and Human Services. 1987), and ELISA positive clones #2 (SEQ ID Nos 6 and 7) and #3 (SEQ ID Nos 8 and 9) from FIG. 2 which confirms the presence of human kappa constant region DNA in-frame with the pelB leader sequence (pelB leader sequence is underlined, the leader sequence cleavage site is indicated by an arrow). The differences in the 5'-end sequence demonstrates that these two clones were selected independently from the library stock. The PCR primer sequence is indicated in bold, clone #2 was originally amplified with CDNAPCRBAK1 and clone #3 was amplified with CDNAPCRBAK2.

FIG. 4 shows the pDM14 N-terminal fusion oestrogen receptor DNA binding domain expression vector nucleotide sequence (SEQ ID No 10), between the HindIII and EcoRI restriction sites, comprising a pelB leader secretion sequence (in italics) (SEQ ID No 11), multiple cloning site containing SfiI and NotI sites, flexible (glycine)$_4$-serine linker sequence (boxed), a fragment of the oestrogen receptor gene comprising amino acids 176-282 (see SEQ ID No 12) of the full length molecule, and the two 38 base pair oestrogen receptor DNA binding domain HRE sequences (HRE 1 and HRE 2).

FIG. 5 shows the pDM16 C-terminal fusion oestrogen receptor DNA binding domain expression vector nucleotide sequence (SEQ ID No 13), between the HindIII and EcoRI restriction sites, comprising a pelB leader secretion sequence (in italics), a fragment of the oestrogen receptor gene comprising amino acids 176-282 (SEQ ID No 14) of the full length molecule, flexible (glycine)$_4$-serine linker sequence (boxed), multiple cloning site containing SfiI and NotI sites and the 38 base pair oestrogen receptor DNA binding domain HRE sequence.

FIG. 9 shows the DNA (SEQ ID Nos 15 and 17) and amino acid (SEQ ID No 16 and 18) sequence of the substance P binding scFv isolated from a human scFv PDCP display library selected against substance P. Heavy chain (SEQ ID Nos 15 and 16) and light chain (SEQ ID Nos 17 and 18) variable region sequence is shown with the CDRs underlined and highlighted in bold.

MATERIALS AND METHODS

Figure 2:
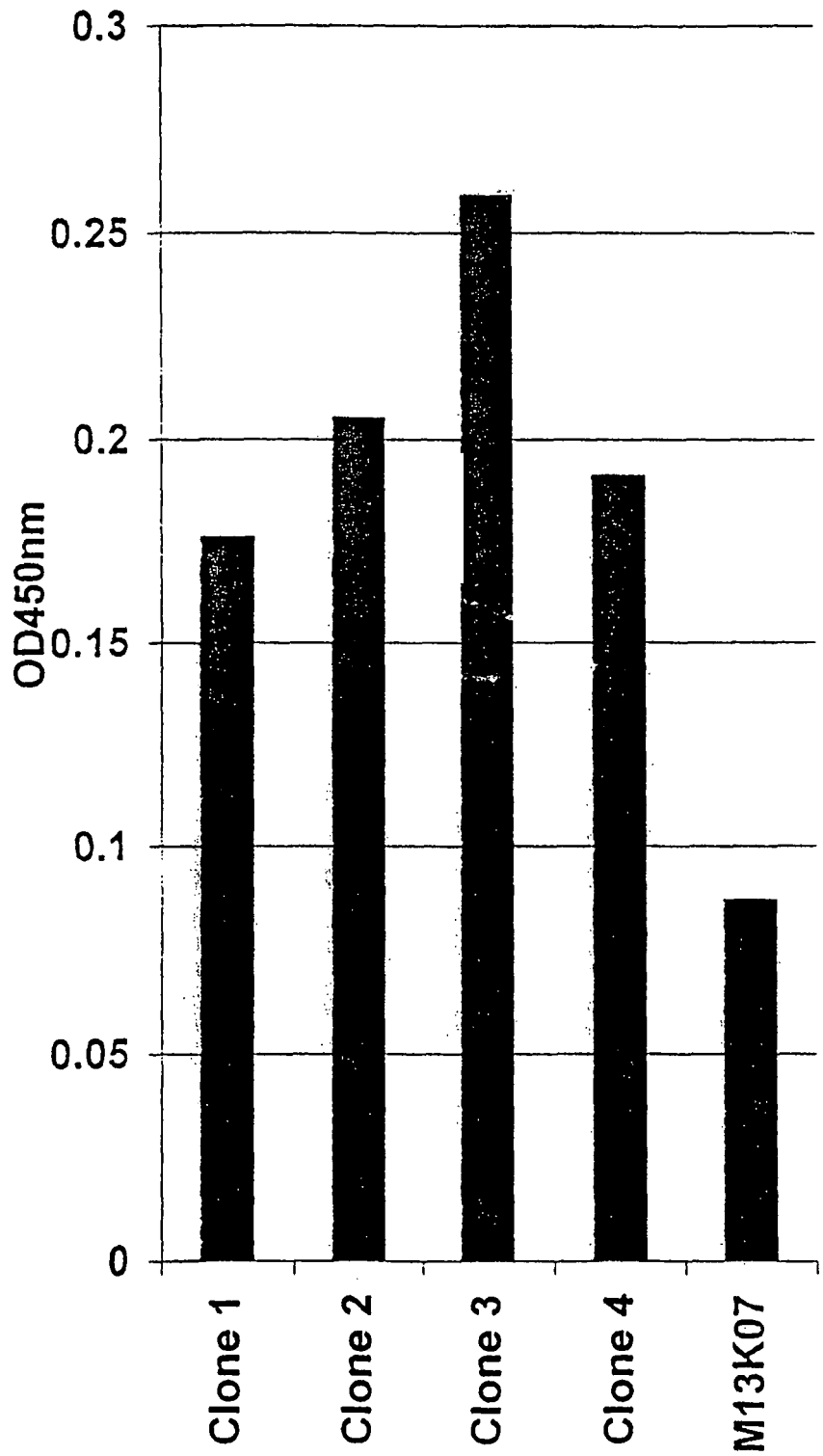
FIG. 2 shows the OD$_{450nm}$ ELISA data for negative control M13K07 phage, and single-clone PDCP display culture supernatants (#1-4, see Example 3) isolated by selection of the lymphocyte cDNA-pDM12 library against anti-human immunoglobulin kappa antibody.

The following procedures used by the present applicant are described in Sambrook, J., et al., 1989 supra.: restriction enzyme digestion, ligation, preparation of electrocompetent cells, electroporation, analysis of restriction enzyme digestion products on agarose gels, DNA purification using phenol/chloroform, preparation of 2×TY medium and plates, preparation of ampicillin, kanamycin, IPTG (Isopropyl β-D-Thiogalactopyranoside) stock solutions, and preparation of phosphate buffered saline.

Restriction enzymes, T4 DNA ligase and cDNA synthesis reagents (Superscript plasmid cDNA synthesis kit) were purchased from Life Technologies Ltd (Paisley, Scotland, U.K.). Oligonucleotides were obtained from Cruachem Ltd (Glasgow, Scotland, U.K.), or Genosys Biotechnologies Ltd (Cambridge, U.K.). Taq DNA polymerase, Wizard SV plasmid DNA isolation kits, streptavidin coated magnetic beads and mRNA isolation reagents (PolyATract 1000) were obtained from Promega Ltd (Southampton, Hampshire, U.K.). Taqplus DNA polymerase was obtained from Stratagene Ltd (Cambridge, U.K.). PBS, BSA, streptavidin, substance P and anti-pan cadherin antibody were obtained from SIGMA Ltd (Poole, Dorset, U.K.). Anti-M13-HRP conjugated antibody, Kanamycin resistant M13K07 helper bacteriophage and RNAguard were obtained from Pharmacia Ltd (St. Albans, Herts, U.K.) and anti-human IgK antibody from Harlan-Seralab (Loughborough, Leicestershire, U.K.) Biotinylated substance P and biotinylated calcitonin gene related peptide (CGRP) were obtained from Peninsula Laboratories (St. Helens, Merseyside, U.K.).

Specific embodiments of the invention are given below in Examples 1 to 9.

EXAMPLE 1

Construction of a N-Terminal PDCP Display Phagemid Vector pDM12

The pDM12 vector was constructed by inserting an oestrogen receptor DNA binding domain, modified by appropriate PCR primers, into a phagemid vector pDM6. The pDM6 vector is based on the pUC119 derived phage display vector pHEN1 (Hoogenboom et al., 1991, Nucleic Acids Res. 19: 4133-4137). It contains $(Gly)_4Ser$ linker, Factor Xa cleavage site, a full length gene III, and streptavidin tag peptide sequence (Schmidt, T. G. and Skerra, A., 1993, Protein Engineering 6: 109-122), all of which can be removed by NotI-EcoRI digestion and agarose gel electrophoresis, leaving a pelB leader sequence, SfiI, NcoI and PstI restriction sites upstream of the digested NotI site. The cloned DNA binding domain is under the control of the lac promoter found in pUC119.

Preparation of pDM6

The pDM12 vector was constructed by inserting an oestrogen receptor DNA binding domain, modified by appropriate PCR primers, into a phagemid vector pDM6. The pDM6 vector is based on the gene pIII phage display vector pHEN1 (Hoogenboom et al., 1991, Nucleic Acids Res. 19: 4133-4137), itself derived from pUC119 (Viera, J. and Messing, J., 1987, Methods in Enzymol. 153: 3-11). It was constructed by amplifying the pIII gene in pHEN1 with two oligonucleotides:

```
                                   (SEQ ID No 19)
PDM6BAK:
5-TTT TCT GCA GTA ATA GGC GGC CGC AGG GGG AGG AGG
GTC CAT CGA AGG TCG CGA AGC AGA GAC TGT TGA AAG T-
3
``` and

```
                                   (SEQ ID No 20)
PDM6FOR:
5-TTT TGA ATT CTT ATT AAC CAC CGA ACT GCG GGT GAC
GCC AAG CGC TTG CGG CCG TTA AGA CTC CTT ATT ACG
CAG-3.
``` and cloning the PstI-EcoRI digested PCR product back into similarly digested pHEN1, thereby removing the c-myc tag sequence and supE TAG codon from pHEN1. The pDM6 vector contains a $(Gly)_4Ser$ linker, Factor Xa cleavage site, a full length gene III, and streptavidin tag peptide sequence (Schmidt, T. G. and Skerra, A., 1993, Protein Engineering 6: 109-122), all of which can be removed by NotI-EcoRI digestion and agarose gel electrophoresis, leaving a pelB leader sequence, SfiI, NcoI and PstI restriction sites upstream of the digested NotI site. The cloned DNA binding domain is under the control of the lac promoter found in pUC119.

The oestrogen receptor DNA binding domain was isolated from cDNA prepared from human bone marrow (Clontech, Palo Alto, Calif., U.S.A.). cDNA can be prepared by many procedures well known to those skilled in the art. As an example, the following method using a Superscript plasmid cDNA synthesis kit can be used:

(a) First Strand Synthesis.

5 µg of bone marrow mRNA, in 5 µl DEPC-treated water was thawed on ice and 2 µl (50 pmol) of cDNA synthesis primer (5'-AAAAGCGGCCGCACTGGCCTGAGAGA $(N)_6$-3') (SEQ ID No 21) was added to the mRNA and the mixture heated to 70° C. for 10 minutes, then snap-chilled on ice and spun briefly to collect the contents to the bottom of the tube. The following were then added to the tube:

| | |
|---|---|
| 1000 u/ml RNAguard | 1 µl |
| 5x first strand buffer | 4 µl |
| 0.1M DTT | 2 µl |
| 10 mM dNTPs | 1 µl |
| 200 u/µl Superscript II reverse transcriptase | 5 µl |

The mixture was mixed by pipetting gently and incubated at 37° C. for 1 hour, then placed on ice.

(b) Second Strand Synthesis.

The following reagents were added to the first strand reaction:

| | |
|---|---|
| DEPC-treated water | 93 µl |
| 5x second strand buffer | 30 µl |
| 10 mM dNTPs | 3 µl |
| 10 u/µl E. coli DNA ligase | 1 µl |
| 10 u/µl E. coli DNA polymerase | 4 µl |
| 2 u/µl E. coli RNase H | 1 µl |

The reaction was vortex mixed and incubated at 16° C. for 2 hours. 2 µl (10u) of T4 DNA polymerase was added and incubation continued at 16° C. for 5 minutes. The reaction was placed on ice and 10 µl 0.5M EDTA added, then phenol-chloroform extracted, precipitated and vacuum dried.

(c) Sal I Adaptor Ligation.

The cDNA pellet was resuspended in 25 µl DEPC-treated water, and ligation set up as follows.

| | |
|---|---|
| cDNA | 25 µl |
| 5x T4 DNA ligase buffer | 10 µl |
| 1 µg/µl Sal I adapters* | 10 µl |
| 1 u/µlT4 DNA ligase | 5 µl |
| *Sal I adapters: | |
| TCGACCCACGCGTCCG-3' | (SEQ ID No 22) |
| GGGTGCCGAGGC-5' | (SEQ ID No 23) |

The ligation was mixed gently and incubated for 16 hours at 16° C., then phenol-chloroform extracted, precipitated and vacuum dried. The cDNA/adaptor pellet was resuspended in 41 µl of DEPC-treated water and digested with 60 units of NotI at 37° C. for 2 hours, then phenol-chloroform extracted, precipitated and vacuum dried. The cDNA pellet was redissolved in 100 µl TEN buffer (10 mM Tris pH 7.5, 0.1 mM EDTA, 25 mM NaCl) and size fractionated using a Sephacryl S-500 HR column to remove unligated adapters and small cDNA fragments (<400 bp) according to the manufacturers instructions. Fractions were checked by agarose gel electrophoresis and fractions containing cDNA less than 400 base pairs discarded, while the remaining fractions were pooled.

(d) PCR Amplification of Oestrogen Receptor DNA Binding Domain.

The oestrogen receptor was PCR amplified from 5 µl (150-250 ng) of bone marrow cDNA using 25 pmol of each of the primers pDM12FOR (SEQ ID No 24) (5'-AAAAGAATTCT-GAATGTGTTATTTTAGCTCAGGT-CACTCTGACCTGATTATCAAGAC-CCCACTTCACCCCCT) and pDM12BAK (SEQ ID No 25) (5'-AAAAGCGGCCGCAGGGGGAGGAGGGTC-CATGGAATCTGCCAAGGAG-3') in two 50 µl reactions containing 0.1 mM dNTPs, 2.5 units Taq DNA polymerase, and 1×PCR reaction buffer (10 mM Tris-HCl pH 9.0, 5 mM KCl, 0.01% Triton X®-100, 1.5 mM MgCl$_2$) (Promega Ltd, Southampton, U.K.). The pDM12FOR primer anneals to the 3'-end of the DNA binding domain of the oestrogen receptor and incorporates two stop codons, the 38 base pair consensus oestrogen receptor HRE sequence, and an EcoRI restriction site. The pDM12BAK primer anneals to the 5'-end of the DNA binding domain of the oestrogen receptor and incorporates the (Gly)$_4$Ser linker and the NotI restriction site.

Reactions were overlaid with mineral oil and PCR carried out on a Techne PHC-3 thermal cycler for 30 cycles of 94° C., 1 minute; 65° C., 1 minute; 72° C., 1 minute. Reaction products were electrophoresed on an agarose gel, excised and products purified from the gel using a Geneclean II kit according to the manufacturers instructions (Bio101, La Jolla, Calif., U.S.A.).

(e) Restriction Digestion and Ligation.

The PCR reaction appended NotI and EcoRI restriction sites, the (Gly)$_4$Ser linker, stop codons and the 38 base pair oestrogen receptor target HRE nucleotide sequence to the oestrogen receptor DNA binding domain sequence (see FIG. 1). The DNA PCR fragment and the target pDM6 vector (approximately 500 ng) were NotI and EcoRI digested for 1 hour at 37° C., and DNA purified by agarose gel electrophoresis and extraction with Geneclean II kit (Bio101, La Jolla, Calif., U.S.A.). The oestrogen receptor DNA binding domain cassette was ligated into the NotI-EcoRI digested pDM6 vector overnight at 16° C., phenol/chloroform extracted and precipitated then electroporated into TG1 E. coli (genotype: K12, (Δlac-pro), supE, thi, hsD5/F'traD36, proA$^+$B$^+$, LacI$^q$, LacZΔ15) and plated onto 2×TY agar plates supplemented with 1% glucose and 100 µg/ml ampicillin. Colonies were allowed to grow overnight at 37° C. Individual colonies were picked into 5 ml 2×TY supplemented with 1% glucose and 100 µg/ml ampicillin and grown overnight at 37° C. Double stranded phagemid DNA was isolated with a Wizard SV plasmid DNA isolation kit and the sequence confirmed with a Prism dyedeoxy cycle sequencing kit (Perkin-Elmer, Warrington, Lancashire, U.K.) using M13FOR (SEQ ID No 26) (5'-GTAAAACGACGGCCAGT) and M13REV (SEQ ID No 27) (5'-GGATAACAATTTCACACAGG) oligonucleotides. The pDM12 PDCP display vector DNA sequence between the HindIII and EcoRI restriction sites is shown in FIG. 1.

EXAMPLE 2

Insertion of a Random-Primed Human Lymphocyte cDNA into pDM12 and Preparation of a Master PDCP Stock Libraries of peptides can be constructed by many methods known to those skilled in the art. The example given describes a method for constructing a peptide library from randomly primed cDNA, prepared from mRNA isolated from a partially purified cell population.

mRNA was isolated from approximately 10$^9$ human peripheral blood lymphocytes using a polyATract 1000 mRNA isolation kit (Promega, Southampton, UK). The cell pellet was resuspended in 4 ml extraction buffer (4M guanidine thiocyanate, 25 mM sodium citrate pH 7.1, 2% β-mercaptoethanol). 8 ml of pre-heated (70° C.) dilution buffer (6×SSC, 10 mM Tris pH 7.4, 1 mM EDTA, 0.25% SDS, 1% β-mercaptoethanol) was added to the homogenate and mixed thoroughly by inversion. 10 µl of biotinylated oligo-dT (50 pmol/µl) was added, mixed and the mixture incubated at 70° C. for 5 minutes. The lymphocyte cell lysate was transferred to 6×2 ml sterile tubes and spun at 13,000 rpm in a microcentrifuge for ten minutes at ambient temperature to produce a cleared lysate. During this centrifugation, streptavidin coated magnetic beads were resuspended and 6 ml transferred to a sterile 50 ml Falcon tube, then placed in the magnetic stand in a horizontal position until all the beads were captured. The supernatant was carefully poured off and beads resuspended in 6 ml 0.5×SSC, then the capture repeated. This wash was repeated 3 times, and beads resuspended in a final volume of 6 ml 0.5×SSC. The cleared lysate was added to the washed beads, mixed by inversion and incubated at ambient temperature for 2 minutes, then beads captured in the magnetic stand in a horizontal position. The beads were resuspended gently in 2 ml 0.5×SSC and transferred to a sterile 2 ml screwtop tube, then captured again in the vertical position, and the wash solution discarded. This wash was repeated twice more. 1 ml of DEPC-treated water was added to the beads and mixed gently. The beads were again captured and the eluted mRNA transferred to a sterile tube. 50l was electrophoresed to check the quality and quantity of mRNA, while the remainder was precipitated with 0.1 volumes 3M sodium acetate and three volumes absolute ethanol at −80° C. overnight in 4 aliquots in sterile 1.5 ml screwtop tubes.

Double stranded cDNA was synthesised as described in Example 1 using 5 µg of lymphocyte mRNA as template. The cDNA was PCR amplified using oligonucleotides CDNAPCRFOR (SEQ ID No 28) (5'-AAAGCGGCCG-CACTGGCCTGAGAGA), which anneals to the cDNA synthesis oligonucleotide described in Example 1 which is present at the 3'-end of all synthesised cDNA molecules incorporates a NotI restriction site, and an equimolar mixture of CDNAPCRBAK1, CDNAPCRBAK2 and CDNAPCR-BAK3. CDNAPCRBAK1: (SEQ ID No 29) 5'-AAAAGGC-CCAGCCGGCCATGGCCCAGCCCACCACGCGTCCG, CDNAPCRBAK2: (SEQ ID No 30) 5'-AAAAGGCCCAGC-CGGCCATGGCCCAGTCCCACCACGCGTCCG, CDNAPCRBAK3: (SEQ ID No 31) 5'-AAAAGGCCCAGC-CGGCCATGGCCCAGTACCCACCACGCGTCCG), all three of which anneal to the SalI adaptor sequence found at the 5'-end of the cDNA and incorporate a SfiI restriction site at the cDNA 5'-end. Ten PCR reactions were carried out using 2 µl of cDNA (50 ng) per reaction as described in Example 1 using 25 cycles of 94° C., 1 minute; 60° C., 1 minute; 72° C., 2 minutes. The reactions were pooled and a 20 µl aliquot checked by agarose gel electrophoresis, the remainder was phenol/chloroform extracted and ethanol precipitated and resuspended in 100 µl sterile water. 5 µg of pDM12 vector DNA and lymphocyte cDNA PCR product were SfiI-NotI digested phenol/chloroform extracted and small DNA fragments removed by size selection on Chromaspin 1000 spin columns (Clontech, Palo Alto, Calif., U.S.A.) by centrifugation at 700 g for 2 minutes at room temperature. Digested pDM12 and lymphocyte cDNA were ethanol precipitated and ligated together for 16 hours at 16° C. The ligated DNA was precipitated and electroporated in to TG1 *E. coli*. Cells were grown in 1 ml SOC medium per cuvette used for 1 hour at 37° C., and plated onto 2×TY agar plates supplemented with 1% glucose and 100 µg/ml ampicillin. $10^{-4}$, $10^{-5}$ and $10^{-6}$ dilutions of the electroporated bacteria were also plated to assess library size. Colonies were allowed to grow overnight at 30° C. $2\times10^8$ ampicillin resistant colonies were recovered on the agar plates.

The bacteria were then scraped off the plates into 40 ml 2×TY broth supplemented with 20% glycerol, 1% glucose and 100 µg/ml ampicillin. 5 ml was added to a 20 ml 2×TY culture broth supplemented with 1% glucose and 100 µg/ml ampicillin and infected with $10^{11}$ kanamycin resistance units (kru) M13K07 helper phage at 37° C. for 30 minutes without shaking, then for 30 minutes with shaking at 200 rpm. Infected bacteria were transferred to 200 ml 2×TY broth supplemented with 25 µg/ml kanamycin, 100 µg/ml ampicillin, and 20 µM IPTG, then incubated overnight at 37° C., shaking at 200 rpm. Bacteria were pelleted at 4000 rpm for 20 minutes in 50 ml Falcon tubes, and 40 ml 2.5M NaCl/20% PEG 6000 was added to 200 ml of particle supernatant, mixed vigorously and incubated on ice for 1 hour to precipitate PDCP particles. Particles were pelleted at 11000 rpm for 30 minutes in 250 ml Oakridge tubes at 4° C. in a Sorvall RC5B centrifuge, then resuspended in 2 ml PBS buffer after removing all traces of PEG/NaCl with a pipette, then bacterial debris removed by a 5 minute 13500 rpm spin in a microcentrifuge. The supernatant was filtered through a 0.45 µm polysulfone syringe filter and stored at −20° C.

EXAMPLE 3

Isolation of Human Immunoglobulin Kappa Light Chains by Repeated Rounds of Selection Against Anti-Human Kappa Antibody For the first round of library selection a 70×11 mm NUNC Maxisorp Immunotube (Life Technologies, Paisley, Scotland U.K.) was coated with 2.5 ml of 10 µg/ml of anti-human kappa antibody (Seralab, Crawley Down, Sussex, U.K.) in PBS for 2 hours at 37° C. The tube was rinsed three times with PBS (fill & empty) and blocked with 3 ml PBS/2% BSA for 2 hours at 37° C. and washed as before. $4\times10^{12}$ a.r.u. of pDM12-lymphocyte cDNA PDCP stock was added in 2 ml 2% BSA/PBS/0.05% Tween 20, and incubated for 30 minutes on a blood mixer, then for 90 minutes standing at ambient temperature. The tube was washed ten times with PBS/0.1% Tween 20, then a further ten times with PBS only. Bound particles were eluted in 1 ml of freshly prepared 0.1M triethylamine for 10 minutes at ambient temperature on a blood mixer. Eluted particles were transferred to 0.5 ml 1M Tris pH 7.4, vortex mixed briefly and transferred to ice.

Neutralised particles were added to 10 ml log phase TG1 *E. coli* bacteria (optical density: $OD_{600}$ nm 0.3-0.5) and incubated at 37° C. without shaking for 30 minutes, then with shaking at 200 rpm for 30 minutes. $10^{-3}$, $10^{-4}$ & $10^{-5}$ dilutions of the infected culture were prepared to estimate the number of particles recovered, and the remainder was spun at 4000 rpm for 10 minutes, and the pellet resuspended in 300 µl 2×TY medium by vortex mixing. Bacteria were plated onto 2×TY agar plates supplemented with 1% glucose and 100 µg/ml ampicillin. Colonies were allowed to grow overnight at 30° C.

A PDCP stock was prepared from the bacteria recovered from the first round of selection, as described in Example 2 from a 100 ml overnight culture. 250 µl of the round 1 amplified PDCP stock was then selected against anti-human kappa antibody as described above with the tube was washed twelve times with PBS/0.1% Tween 20, then a further twelve times with PBS only.

To identify selected clones, eighty-eight individual clones recovered from the second round of selection were then tested by ELISA for binding to anti-human kappa antibody. Individual colonies were picked into 100 µl 2×TY supplemented with 100 µg/ml ampicillin and 1% glucose in 96-well plates (Costar) and incubated at 37° C. and shaken at 200 rpm for 4 hours. 25 µl of each culture was transferred to a fresh 96-well plate, containing 25 µl/well of the same medium plus $10^7$ k.r.u. M13K07 kanamycin resistant helper phage and incubated at 37° C. for 30 minutes without shaking, then incubated at 37° C. and shaken at 200 rpm for a further 30 minutes. 160 µl of 2×TY supplemented with 100 µg/ml ampicillin, 25 µg/ml kanamycin, and 20 µM IPTG was added to each well and particle amplification continued for 16 hours at 37° C. while shaking at 200 rpm. Bacterial cultures were spun in microtitre plate carriers at 2000 g for 10 minutes at 4° C. in a benchtop centrifuge to pellet bacteria and culture supernatant used for ELISA.

A Dynatech Immulon 4 ELISA plate was coated with 200 ng/well anti-human kappa antibody in 100 µl/well PBS for one hour at 37° C. The plate was washed 2×200 µl/well PBS and blocked for 1 hour at 37° C. with 200 µl/well 2% BSA/PBS and then washed 2×200 µl/well PBS. 50 µl PDCP culture supernatant was added to each well containing 50 µl/well 4% BSA/PBS/0.1% Tween 20, and allowed to bind for 1 hour at ambient temperature. The plate was washed three times with 200 µl/well PBS/0.1% Tween 20, then three times with 200 µl/well PBS. Bound PDCPs were detected with 100 µl/well, 1:5000 diluted anti-M13-HRP conjugate (Pharmacia) in 2% BSA/PBS/0.05% Tween 20 for 1 hour at ambient temperature and the plate washed six times as above. The plate was developed for 5 minutes at ambient temperature with 100 µl/well freshly prepared TMB (3,3',5,5'-Tetramethylbenzidine) substrate buffer (0.005% $H_2O_2$, 0.1 mg/ml TMB in 24 mM citric acid/52 mM sodium phosphate buffer pH 5.2). The reaction was stopped with 100 µl/well 12.5% $H_2SO_4$ and read at 450 nm. (ELISA data for binding clones is shown in FIG. 2). These clones were then sequenced with M13REV primer (SEQ ID No 27) as in Example 1. The sequence of two of the clones isolated is shown in FIG. 3 (see SEQ ID Nos 7 to 10).

EXAMPLE 4

Construction of the pDM14 N-Terminal Display Vector

It would be useful to design vectors that contain a second DBD binding sequence, such as a second oestrogen receptor HRE sequence, thus allowing the display of increased numbers of peptides per PDCP. Peale et al. (1988, Proc. Natl. Acad. Sci. USA 85: 1038-1042) describe a number of oestrogen receptor HRE sequences. These sequences were used to define an HRE sequence, which differs from that cloned in pDM12, which we used to create a second N-terminal display vector (pDM14). The oligonucleotide: 5'-AAAAGAATTC-GAGGTTACATTAACTTTGTTCCGGTCA-GACTGACCCAAGTCGACCTGAATGTGTTATTTTAG-3, (SEQ ID No 32) was synthesised and used to mutagenise pDM12 by PCR with pDM12BAK oligonucleotide as described in Example 1 using 100 ng pDM12 vector DNA as template. The resulting DNA fragment, which contained the oestrogen receptor DBD and two HRE sequences separated by a SalI restriction enzyme site, was NotI-EcoRI restriction enzyme digested and cloned into NotI-EcoRI digested pDM12 vector DNA as described in Example 1 to create pDM14. The sequence of pDM14 between the HindIII and EcoRI restriction enzyme sites was checked by DNA sequencing. The final vector sequence between these two sites is shown in FIG. 4 (see SEQ ID Nos 11 and 12).

EXAMPLE 5

Construction of the pDM16 C-Terminal Display Vector

In order to demonstrate the display of peptides fused to the C-terminus of a DBD on a PDCP a suitable vector, pDM16, was created.

In pDM16 the pelB leader DNA sequence is fused directly to the oestrogen receptor DBD sequence removing the multiple cloning sites and the Gly$_4$Ser linker DNA sequence found in pDM12 and pDM14, which are appended to the C-terminal end of the DBD sequence upstream of the HRE DNA sequence.

To create this vector two separate PCR reactions were carried out on a Techne Progene thermal cycler for 30 cycles of 94° C., 1 minute; 60° C., 1 minute; 72° C., 1 minute. Reaction products were electrophoresed on an agarose gel, excised and products purified from the gel using a Mermaid or Geneclean II kit, respectively, according to the manufacturers instructions (Bio101, La Jolla, Calif., U.S.A.).

In the first, the 5'-untranslated region and pelB leader DNA sequence was amplified from 100 ng of pDM12 vector DNA using 50 pmol of each of the oligonucleotides pelBFOR (SEQ ID No 33) (5'-CCTTGGCAGATTCCATCTCGGCCAT-TGCCGGC-3') and M13REV (SEQ ID NO 27) (see above) in a 100 µl reaction containing 0.1 mM dNTPs, 2.5 units Taqplus DNA polymerase, and 1× High Salt PCR reaction buffer (20 mM Tris-HCl pH 9.2, 60 mM KCl, 2 mM MgCl$_2$) (Stratagene Ltd, Cambridge, U.K.).

In the second, the 3'-end of the pelB leader sequence and the oestrogen receptor DBD was amplified from 100 ng of pDM12 vector DNA using 50 pmol of each of the oligonucleotides pelBBAK (SEQ ID No 34) (5'-CCGGCAATGGC-CGAGATGGAATCTGCCAAGG-3') and pDM16FOR (SEQ ID No 35) (5'-TTTTGTCGACTCAATCAGTTAT-GCGGCCGCCAGCTGCAGGAGGGCCG-GCTGGGCCGACCCTCCTCCCCCAGAC-CCCACTTCACCCC-3') in a 100 µl reaction containing 0.1 mM dNTPs, 2.5 units Taqplus DNA polymerase, and 1× High Salt PCR reaction buffer (Stratagene Ltd, Cambridge, U.K.). Following gel purification both products were mixed together and a final round of PCR amplification carried out to link the two products together as described above, in a 100 µl reaction containing 0.1 mM dNTPs, 2.5 units Taq DNA polymerase, and 1×PCR reaction buffer (10 mM Tris-HCl pH 9.0, 5 mM KCl, 0.01% Triton X®-100, 1.5 mM MgCl$_2$) (Promega Ltd, Southampton, U.K.).

The resulting DNA fragment, was HindIII-SalI restriction enzyme digested and cloned into HindIII-SalI digested pDM14 vector DNA as described in Example 1 to create pDM16. The sequence of pDM16 between the HindIII and EcoRI restriction enzyme sites was checked by DNA sequencing. The final vector sequence between these two sites is shown in FIG. 5 (see SEQ ID Nos 13 and 14).

EXAMPLE 6

Display of the C-Terminal Fragment of Human N-Cadherin on the Surface of a PDCP cDNA libraries of peptides can be constructed by many methods known to those skilled in the art. One commonly used method for constructing a peptide library uses oligo dT primed cDNA, prepared from polyA+ mRNA. In this method the first-strand synthesis is carried out using an oligonucleotide which anneals to the 3'-end polyA tail of the mRNA composed of $T_n$ (where n is normally between 10 and 20 bases) and a restriction enzyme site such as NotI to facilitate cloning of cDNA. The cDNA cloned by this method is normally composed of the polyA tail, the 3'-end untranslated region and the C-terminal coding region of the protein. As an example of the C-terminal display of peptides on a PDCP, a human cDNA isolated from a library constructed by the above method was chosen.

The protein N-cadherin is a cell surface molecule involved in cell-cell adhesion. The C-terminal cytoplasmic domain of the human protein (Genbank database accession number: M34064) is recognised by a commercially available monoclonal antibody which was raised against the C-terminal 23 amino acids of chicken N-cadherin (SIGMA catalogue number: C-1821). The 1.4 kb human cDNA fragment encoding the C-terminal 99 amino acids, 3'-untranslated region and polyA tail (NotI site present at the 3'-end of the polyA tail) was amplified from approximately 20 ng pDM7-NCAD#C with 25 pmol of each oligonucleotide M13FOR (SEQ ID No 26) and CDNPCRBAK1 (SEQ ID No 29) (see above) in a 501 reaction containing 0.1 mM dNTPs, 2.5 units Taqplus DNA polymerase, and 1× High Salt PCR reaction buffer (20 mM Tris-HCl pH 9.2, 60 mM KCl, 2 mM MgCl$_2$) (Stratagene Ltd, Cambridge, U.K.) on a Techne Progene thermal cycler for 30 cycles of 94° C., 1 minute; 60° C., 1 minute; 72° C., 1 minute. Following gel purification and digestion with SfiI and NotI restriction enzymes, the PCR product was cloned into pDM16 using an analogous protocol as described in Example 1.

Clones containing inserts were identified by ELISA of 96 individual PDCP cultures prepared as described in Example 3. A Dynatech Immulon 4 ELISA plate was coated with 1:250 diluted anti-pan cadherin monoclonal antibody in 100 µl/well PBS overnight at 4° C. The plate was washed 3×200 µl/well PBS and blocked for 1 hour at 37° C. with 200 µl/well 2% Marvel non-fat milk powder/PBS and then washed 2×200 µl/well PBS. 50 µl PDCP culture supernatant was added to each well containing 50 µl/well 4% Marvel/PBS, and allowed to bind for 1 hour at ambient temperature. The plate was washed three times with 200 µl/well PBS/0.1% Tween 20, then three times with 200 µl/well PBS. Bound PDCPs were detected with 100 µl/well, 1:5000 diluted anti-M13-HRP conjugate (Pharmacia) in 2% Marvel/PBS for 1 hour at ambient temperature and the plate washed six times as above. The plate was developed for 15 minutes at ambient temperature with 100 µl/well freshly prepared TMB (3,3',5,5'-Tetramethylbenzidine) substrate buffer (0.005% $H_2O_2$, 0.1 mg/ml TMB in 24 mM citric acid/52 mM sodium phosphate buffer pH 5.2). The reaction was stopped with 100 µl/well 12.5% $H_2SO_4$ and read at 450 nm. The nucleotide sequence of an ELISA positive clone insert and DBD junction was checked by DNA sequencing using oligonucleotides M13FOR (SEQ ID No 26) (see Example 1) and ORSEQBAK (SEQ ID No 36) (5'-TGTTGAAACACAAGCGCCAG-3').

A fifty-fold concentrated stock of C-terminal N-cadherin PDCP particles was prepared by growing the un-infected TG1 clone in 1 ml 2×TY culture broth supplemented with 1% glucose and 100 g/ml ampicillin for five hours at 37° C., shaking at 200 rpm and infecting with 108 kanamycin resistance units (kru) M13K07 helper phage at 37° C. for 30 minutes without shaking, then for 30 minutes with shaking at 200 rpm. Infected bacteria were transferred to 20 ml 2×TY broth supplemented with 25 µg/ml kanamycin, 100 g/ml ampicillin, and 20 µM IPTG, then incubated overnight at 30° C., shaking at 200 rpm. Bacteria were pelleted at 4000 rpm for 20 minutes in 50 ml Falcon tubes, and 4 ml 2.5M NaCl/20% PEG 6000 was added to 20 ml of PDCP supernatant, mixed vigorously and incubated on ice for 1 hour to precipitate particles.

Figure 6:
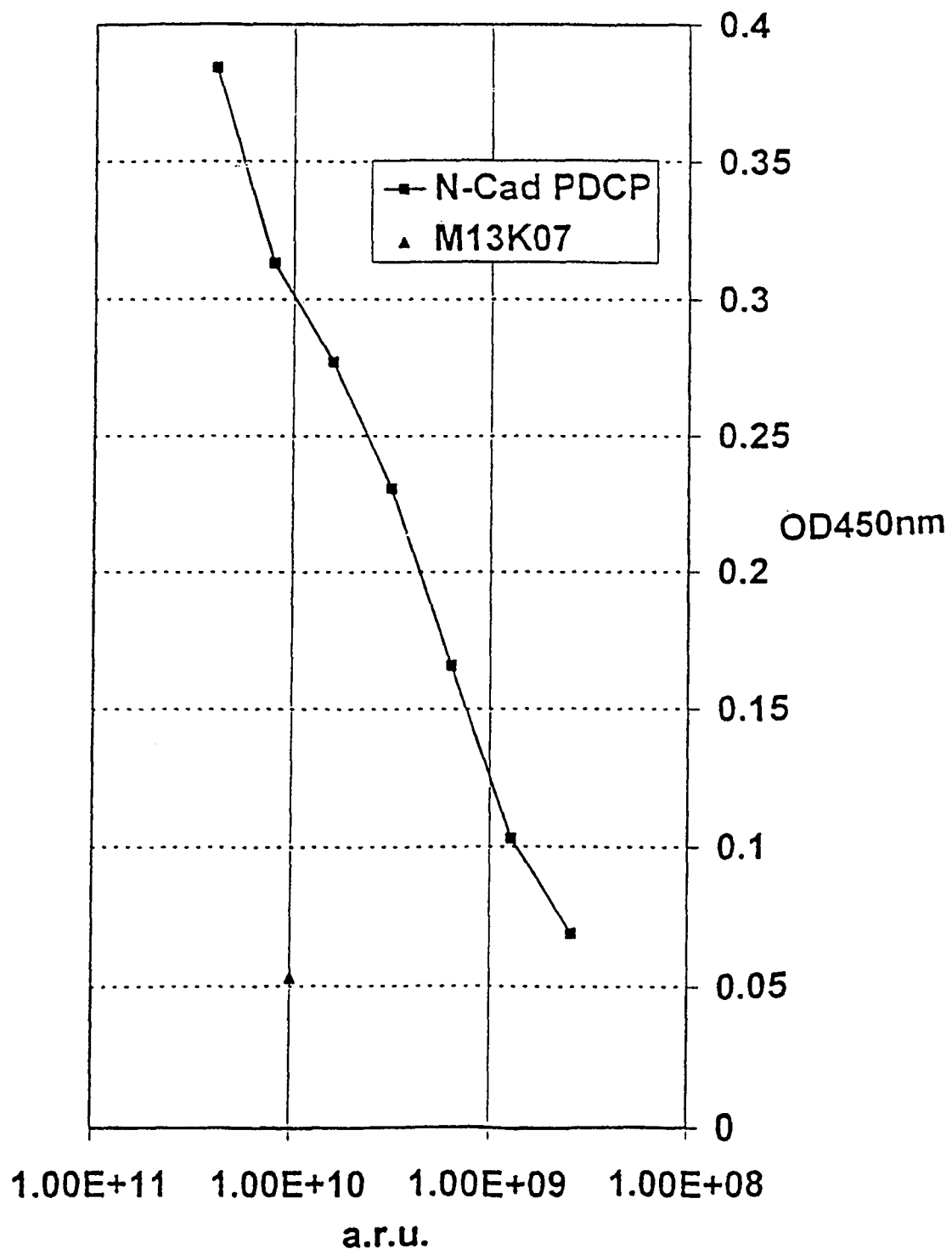
FIG. 6 shows the OD$_{450nm}$ ELISA data for N-cadherin-pDM16 C-terminal display PDCP binding to anti-pan-cadherin monoclonal antibody in serial dilution ELISA as ampicillin resistance units (a.r.u.). Background binding of negative control M13K07 helper phage is also shown.

The particles were pelleted at 11000 rpm for 30 minutes in 50 ml Oakridge tubes at 4° C. in a Sorvall RC5B centrifuge, then resuspended in PBS buffer after removing all traces of PEG/NaCl with a pipette, then bacterial debris removed by a 5 minute 13500 rpm spin in a microcentrifuge. The supernatant was filtered through a 0.45 µm polysulfone syringe filter. The concentrated stock was two-fold serially diluted and used in ELISA against plates coated with anti-pan-cadherin antibody as described above (see FIG. 6).

This example demonstrates the principle of C-terminal display using PDCPs, that C-terminal DBD-peptide fusion PDCPs can be made which can be detected in ELISA, and the possibility that oligo dT primed cDNA libraries may be displayed using this method.

EXAMPLE 7

Display of In Vivo Biotinylated C-Terminal Domain of Human Propionyl CoA Carboxylase on the Surface of a PDCP Example 6 shows that the C-terminal domain of human N-cadherin can be expressed on the surface of a PDCP as a C-terminal fusion with the DBD. Here it is shown that the C-terminal domain of another human protein propionyl CoA carboxylase alpha chain (Genbank accession number: X14608) can similarly be displayed, suggesting that this methodology may be general.

The alpha sub-unit of propionyl CoA carboxylase alpha chain (PCC) contains 703 amino acids and is normally biotinylated at position 669. It is demonstrated that the PCC peptide displayed on the PDCP is biotinylated, as has been shown to occur when the protein is expressed in bacterial cells (Leon-Del-Rio & Gravel; 1994, J. Biol. Chem. 37, 22964-22968).

The 0.8 kb human cDNA fragment of PCC alpha encoding the C-terminal 95 amino acids, 3'-untranslated region and polyA tail (NotI site present at the 3'-end of the polyA tail) was amplified and cloned into pDM16 from approximately 20 ng pDM7-PCC#C with 25 pmol of each oligonucleotide M13FOR (SEQ ID No 26) and CDNPCRBAK1 (SEQ ID No 29) as described in Example 6.

Figure 7:
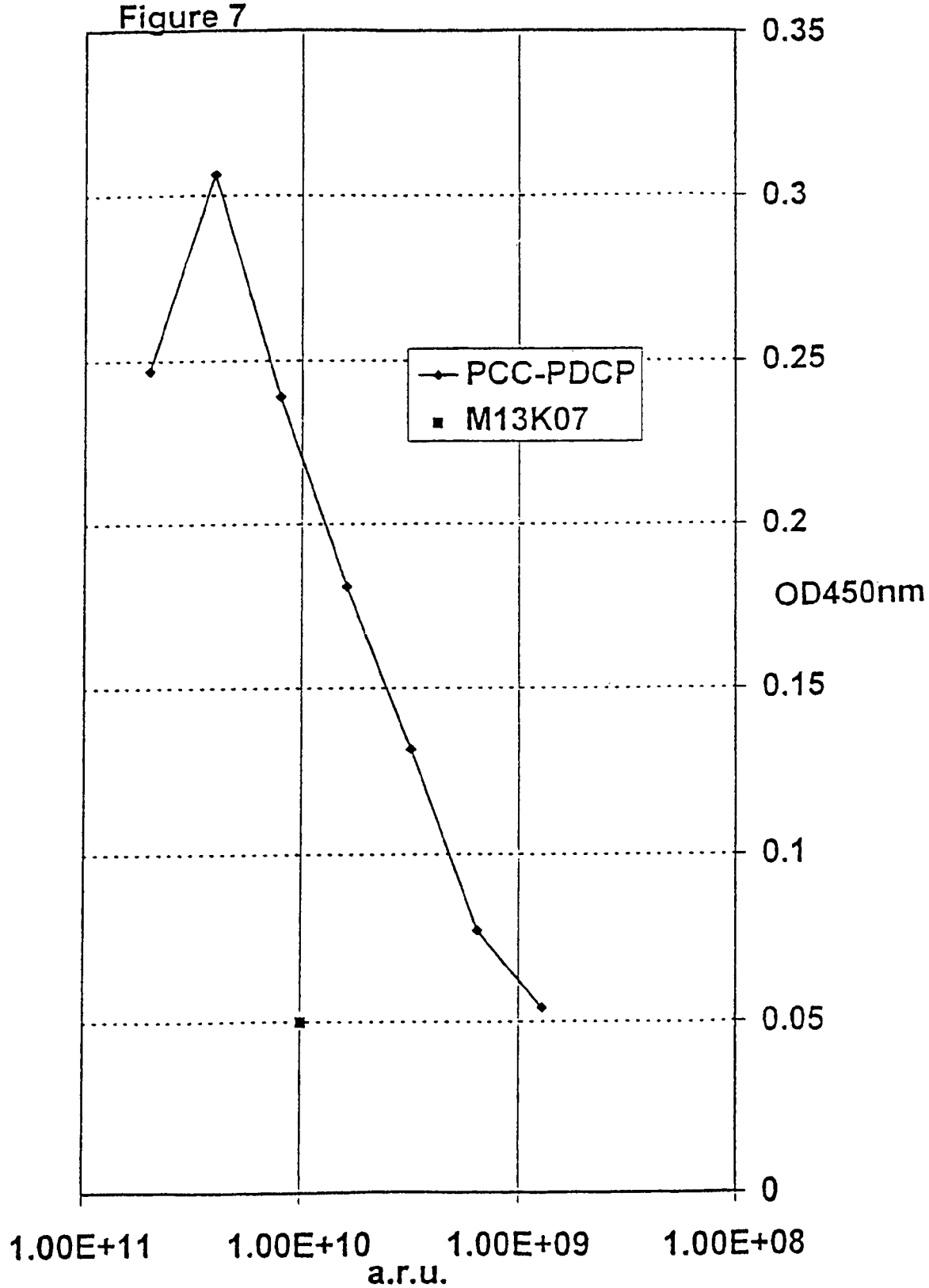
FIG. 7 shows the OD$_{450nm}$ ELISA data for in vivo biotinylated PCC-pDM16 C-terminal display PDCP binding to streptavidin in serial dilution ELISA as ampicillin resistance units (a.r.u.). Background binding of negative control M13K07 helper phage is also shown.

Clones containing inserts were identified by ELISA as described in Example 6, except that streptavidin was coated onto the ELISA plate at 250 ng/well, in place of the anti-cadherin antibody. The nucleotide sequence of an ELISA positive clone insert and DBD junction was checked by DNA sequencing using oligonucleotides M13FOR (SEQ ID No 26) and ORSEQBAK (SEQ ID No 36) (see above). A fifty-fold concentrated stock of C-terminal PCC PDCP particles was prepared and tested in ELISA against streptavidin as described in Example 6 (see FIG. 7).

This example shows not only that the peptide can be displayed as a C-terminal fusion on a PDCP, but also that in vivo modified peptides can be displayed.

EXAMPLE 8

Construction of a Human scFv PDCP Display Library

This example describes the generation of a human antibody library of scFvs made from an un-immunised human.

The overall strategy for the PCR assembly of scFv fragments is similar to that employed by Marks, J. D. et al. 1991, J. Mol. Biol. 222: 581-597. The antibody gene oligonucleotides used to construct the library are derived from the Marke et al., paper and from sequence data extracted from the Kabat database (Kabat, E. A. et al., Sequences of Proteins of Immunological Interest. 4$^{th}$ edition. U.S. Department of Health and Human Services. 1987). The three linker oligonucleotides are described by Zhou et al. (1994, Nucleic Acids Res., 22: 888-889), all oligonucleotides used are detailed in Table 1.

First, mRNA was isolated from peripheral blood lymphocytes and cDNA prepared for four repertoires of antibody genes IgD, IgM, Igκ, and Igλ, using four separate cDNA synthesis primers. VH genes were amplified from IgD and IgM primed cDNA, and VL genes were amplified from Igκ and Igλ primed cDNA. A portion of each set of amplified heavy chain or light chain DNA was then spliced with a separate piece of linker DNA encoding the 15 amino acids (Gly$_4$ Ser)$_3$ (Huston, J. S. et al. 1989, Gene, 77: 61). The 3'-end of the VH PCR products and the 5'-end of the VL PCR products overlap the linker sequence as a result of incorporating linker sequence in the JH, Vκ and Vλ family primer sets (Table 1). Each VH-linker or linker-VL DNA product was then spliced with either VH or VL DNA to produce the primary scFv product in a VH-linker-VL configuration. This scFv product was then amplified and cloned into pDM12 as a SfiI-NotI fragment, electroporated into TG1 and a concentrated PDCP stock prepared.

mRNA Isolation and cDNA Synthesis.

Human lymphocyte mRNA was purified as described in Example 2. Separate cDNA reactions were performed with IGDCDNAFOR (SEQ ID No 37), IGMCDNAFOR (SEQ ID No 38), IGKCDNAFOR (SEQ ID No 39) and IGλCDNAFOR (SEQ ID No 40) oligonucleotides. 50 pmol of each primer was added to approximately 5 µg of mRNA in 20 µl of nuclease free water and heated to 70° C. for 5 minutes and cooled rapidly on ice, then made up to a final reaction volume of 100 µl containing 50 mM Tris pH 8.3, 75 mM KCl, 3 mM MgCl$_2$, 10 mM DTT, 0.5 mM dNTPs, and 2000 units of Superscript II reverse transcriptase (Life Technologies, Paisley, Scotland, U.K.). The reactions were incubated at 37° C. for two hours, then heated to 95° C. for 5 minutes.

Primary PCRs.

For the primary PCR amplifications separate amplifications were set up for each family specific primer with either an equimolar mixture of the JHFOR primer set (SEQ ID Nos 41 to 44) for IgM and IgD cDNA, or with SCFVKFOR (SEQ ID No 51) or SCFVXFOR (SEQ ID No 52) for IgK or Igλ cDNA respectively e.g. VH1BAK and JHFOR set; Vκ2BAK (SEQ ID No 54) and SCFVκFOR (SEQ ID No 51); Vλ3aBAK (SEQ ID No 66) and SCFVλFOR (SEQ ID No 52) etc. Thus, for IgM, IgD and Igκ cDNA six separate reactions were set up, and seven for Igλ cDNA. A 50 µl reaction mixture was prepared containing 2 µl cDNA, 25 pmol of the appropriate FOR and BAK primers, 0.1 mM dNTPs, 2.5 units Taqplus DNA polymerase, and 1× High Salt PCR reaction buffer (20 mM Tris-HCl pH 9.2, 60 mM KCl, 2 mM MgCl$_2$) (Stratagene Ltd, Cambridge, U.K.). Reactions were amplified on a Techne Progene thermal cycler for 30 cycles of 94° C., 1 minute; 60° C., 1 minute; 72° C., 2 minutes, followed by 10 minutes at 72° C. Fifty microliters of all 25 reaction products were electrophoresed on an agarose gel, excised and products purified from the gel using a Geneclean II kit according to the manufacturers instructions (Bio101, La Jolla, Calif., U.S.A.). All sets of IgD, IgM, IgK or Igλ reaction products were pooled to produce VH or VL DNA sets for each of the four repertoires. These were then adjusted to approximately 20 ng/µl.

Preparation of Linker.

Linker product was prepared from eight 100 µl reactions containing 5 ng LINKAMP3T (SEQ ID No 76) template oligonucleotide, 50 pmol of LINKAMP3 (SEQ ID No 74) and LINKAMP5 (SEQ ID No 75) primers, 0.1 mM dNTPs, 2.5 units Taqplus DNA polymerase, and 1× High Salt PCR reaction buffer (20 mM Tris-HCl pH 9.2, 60 mM KCl, 2 mM $MgCl_2$) (Stratagene Ltd, Cambridge, U.K.). Reactions were amplified on a Techne Progene thermal cycler for 30 cycles of 94° C., 1 minute; 60° C., 1 minute; 72° C., 1 minute, followed by 10 minutes at 72° C. All reaction product was electrophoresed on a 2% low melting point agarose gel, excised and products purified from the gel using a Mermaid kit according to the manufacturers instructions (Bio101, La Jolla, Calif., U.S.A.) and adjusted to 5 ng/µl.

First Stage Linking.

Four linking reactions were prepared for each repertoire using 20 ng of VH or VL DNA with 5 ng of Linker DNA in 100 µl reactions containing (for IgM or IgD VH) 50 pmol of LINKAMPFOR and VH1-6BAK set, or, 50 pmol LINKA-MPBAK and either SCFVκFOR (Igκ) or SCFVλFOR (Igλ), 0.1 mM dNTPs, 2.5 units Taq DNA polymerase, and 1×PCR reaction buffer (10 mM Tris-HCl pH 9.0, 5 mM KCl, 0.01% Triton X®-100, 1.5 mM $MgCl_2$) (Promega Ltd, Southampton, U.K.). Reactions were amplified on a Techne Progene thermal cycler for 30 cycles of 94° C., 1 minute; 60° C., 1 minute; 72° C., 2 minutes, followed by 10 minutes at 72° C. Reaction products were electrophoresed on an agarose gel, excised and products purified from the gel using a Geneclean II kit according to the manufacturers instructions (Bio101, La Jolla, Calif., U.S.A.) and adjusted to 20 ng/µl.

Final Linking and Reamplification.

To prepare the final scFv DNA products, five 100 µl reactions were performed for VH-LINKER plus VL DNA, and, five 100 µl reactions were performed for VH plus LINKER-VL DNA for each of the four final repertoires (IgM VH-VK, VH-Vλ; IgD VH-VK, VH-Vλ) as described in step (d) above using 20 ng of each component DNA as template. Reaction products were electrophoresed on an agarose gel, excised and products purified from the gel using a Geneclean II kit according to the manufacturers instructions (Bio101, La Jolla, Calif., U.S.A.) and adjusted to 20 ng/µl. Each of the four repertoires was then re-amplified in a 100 µl reaction volume containing 2 ng of each linked product, with 50 pmol VHBAK1-6 (SEQ ID Nos 53 to 58) and either the JKFOR (SEQ ID Nos 66 to 70) or JλFOR (SEQ ID Nos 71 to 73) primer sets, in the presence of 0.1 mM dNTPs, 2.5 units Taq DNA polymerase, and 1×PCR reaction buffer (10 mM Tris-HCl pH 9.0, 5 mM KCl, 0.01% Triton XO-100, 1.5 mM $MgCl_2$) (Promega Ltd, Southampton, U.K.). Thirty reactions were performed per repertoire to generate enough DNA for cloning. Reactions were amplified on a Techne Progene thermal cycler for 25 cycles of 94° C., 1 minute; 65° C., 1 minute; 72° C., 2 minutes, followed by 10 minutes at 72° C. Reaction products were phenol-chloroform extracted, ethanol precipitated, vacuum dried and re-suspended in 80 µl nuclease free water.

Cloning into pDM12.

Each of the four repertoires was SfiI-NotI digested, and electrophoresed on an agarose gel, excised and products purified from the gel using a Geneclean II kit according to the manufacturers instructions (Bio101, La Jolla, Calif., U.S.A.). Each of the four repertoires was ligated overnight at 16° C. in 140 µl with 10 µg of SfiI-NotI cut pDM12 prepared as in Example 2, and 12 units of T4 DNA ligase (Life Technologies, Paisley, Scotland, U.K.). After incubation the ligations were adjusted to 200 µl with nuclease free water, and DNA precipitated with 1 µl 20 mg/ml glycogen, 100 µl 7.5M ammonium acetate and 900 µl ice-cold (−20° C.) absolute ethanol, vortex mixed and spun at 13,000 rpm for 20 minutes in a microfuge to pellet DNA. The pellets were washed with 500 µl ice-cold 70% ethanol by centrifugation at 13,000 rpm for 2 minutes, then vacuum dried and re-suspended in 10 µl DEPC-treated water. 1 µl aliquots of each repertoire was electroporated into 80 µl $E.$ $coli$ (TG1). Cells were grown in 1 ml SOC medium per cuvette used for 1 hour at 37° C., and plated onto 2×TY agar plates supplemented with 1% glucose and 100 µg/ml ampicillin. $10^{-4}$, $10^{-5}$ and $10^{-6}$ dilutions of the electroporated bacteria were also plated to assess library size. Colonies were allowed to grow overnight at 30° C. Cloning into SfiI-NotI digested pDM12 yielded an IgM-κ/λ repertoire of $1.16 \times 10^9$ clones, and an IgD-κ/λ repertoire of $1.21 \times 10^9$ clones.

Preparation of PDCP Stock.

Separate PDCP stocks were prepared for each repertoire library. The bacteria were then scraped off the plates into 30 ml 2×TY broth supplemented with 20% glycerol, 1% glucose and 100 µg/ml ampicillin. 3 ml was added to a 50 ml 2×TY culture broth supplemented with 1% glucose and 100 g/ml ampicillin and infected with $10^{11}$ kanamycin resistance units (kru) M13K07 helper phage at 37° C. for 30 minutes without shaking, then for 30 minutes with shaking at 200 rpm. Infected bacteria were transferred to 500 ml 2×TY broth supplemented with 25 µg/ml kanamycin, 100 µg/ml ampicillin, and 20 µM IPTG, then incubated overnight at 30° C., shaking at 200 rpm. Bacteria were pelleted at 4000 rpm for 20 minutes in 50 ml Falcon tubes, and 80 ml 2.5M NaCl/20% PEG 6000 was added to 400 ml of particle supernatant, mixed vigorously and incubated on ice for 1 hour to precipitate PDCP particles. Particles were pelleted at 11000 rpm for 30 minutes in 250 ml Oakridge tubes at 4° C. in a Sorvall RC5B centrifuge, then resuspended in 40 ml water and 8 ml 2.5M NaCl/20% PEG 6000 added to reprecipitate particles, then incubated on ice for 20 minutes. Particles were again pelleted at 11000 rpm for 30 minutes in 50 ml Oakridge tubes at 4° C. in a Sorvall RC5B centrifuge, then resuspended in 5 ml PBS buffer, after removing all traces of PEG/NaCl with a pipette. Bacterial debris was removed by a 5 minute 13500 rpm spin in a microcentrifuge. The supernatant was filtered through a 0.45 µm polysulfone syringe filter, adjusted to 20% glycerol and stored at −70° C.

EXAMPLE 9

Isolation of Binding Activity from a N-Terminal Display PDCP Library of Human scFvs The ability to select binding activities to a target of interest from a human antibody library is important due to the possibility of generating therapeutic human antibodies. In addition, such libraries allow the isolation of antibodies to targets which cannot be used for traditional methods of antibody generation due to toxicity, low immunogenicity or ethical considerations. In this example we demonstrate the isolation of specific binding activities against a peptide antigen from a PDCP library of scFvs from an un-immunised human.

The generation of the library, used for the isolation of binding activities in this example, is described in Example 8.

Substance P is an eleven amino acid neuropeptide involved in inflammatory and pain responses in vivo. It has also been implicated in a variety of disorders such as psoriasis and asthma amongst others (Misery, L. 1997, Br. J. Dertmatol., 137: 843-850; Maggi, C. A. 1997, Regul. Pept. 70: 75-90; Choi, D. C. & Kwon, O. J., 1998, Curr. Opin. Pulm. Med., 4: 16-24). Human antibodies which neutralise this peptide may therefore have some therapeutic potential. As this peptide is too small to coat efficiently on a tube, as described in Example 3, selection of binding activities was performed in-solution, using N-terminal biotinylated substance P and capturing bound PDCP particles on streptavidin-coated magnetic beads.

Enrichment for Substance P Binding PDCP Particles.

An aliquot of approximately $10^{13}$ a.r.u. IgM and IgD scFv library stock was mixed with 1 µg biotinylated substance P in 800 µl 4% BSA/0.1% Tween 20/PBS, and allowed to bind for two hours at ambient temperature. Bound PDCPs were then captured onto 1 ml of BSA blocked streptavidin coated magnetic beads for 10 minutes at ambient temperature. The beads were captured to the side of the tube with a magnet (Promega), and unbound material discarded. The beads were washed eight times with 1 ml PBS/0.1% Tween 20/10 µg/ml streptavidin, then two times with 1 ml of PBS by magnetic capture and removal of wash buffer. After the final wash bound PDCPs were eluted with 1 ml of freshly prepared 0.1M triethylamine for 10 minutes, the beads were captured, and eluted particles transferred to 0.5 ml 1M Tris-HCl pH 7.4. Neutralised particles were added to 10 ml log phase TG1 *E. coli* bacteria and incubated at 37° C. without shaking for 30 minutes, then with shaking at 200 rpm for 30 minutes. $10^{-3}$, $10^{-4}$ & $10^{-5}$ dilutions of the infected culture were prepared to estimate the number of particles recovered, and the remainder was spun at 4000 rpm for 10 minutes, and the pellet resuspended in 300 µl 2×TY medium by vortex mixing. Bacteria were plated onto 2×TY agar plates supplemented with 1% glucose and 100 g/ml ampicillin. Colonies were allowed to grow overnight at 30° C. A 100-fold concentrated PDCP stock was prepared from a 200 ml amplified culture of these bacteria as described above, and 0.5 ml used in as second round of selection with 500 ng biotinylated substance P. For this round 100 µg/ml streptavidin was included in the wash buffer.

ELISA Identification of Binding Clones.

Binding clones were identified by ELISA of 96 individual PDCP cultures prepared as described in Example 3 from colonies recovered after the second round of selection. A Dynatech Immulon 4 ELISA plate was coated with 200 ng/well streptavidin in 100 µl/well PBS for 1 hour at 37° C. The plate was washed 3×200 µl/well PBS and incubated with long/well biotinylated substance P in 100 µl/well PBS for 30 minutes at 37° C. The plate was washed 3×200 µl/well PBS and blocked for 1 hour at 37° C. with 200 µl/well 2% Marvel non-fat milk powder/PBS and then washed 2×200 µl/well PBS. 50 µl PDCP culture supernatant was added to each well containing 50 µl/well 4% Marvel/PBS, and allowed to bind for 1 hour at ambient temperature. The plate was washed three times with 200 µl/well PBS/0.1% Tween 20, then three times with 200 µl/well PBS. Bound PDCPs were detected with 100 µl/well, 1:5000 diluted anti-M13-HRP conjugate (Pharmacia) in 2% Marvel/PBS for 1 hour at ambient temperature and the plate washed six times as above. The plate was developed for 10 minutes at ambient temperature with 100 µl/well freshly prepared TMB (3,3',5,5'-Tetramethylbenzidine) substrate buffer (0.005% $H_2O_2$, 0.1 mg/ml TMB in 24 mM citric acid/52 mM sodium phosphate buffer pH 5.2). The reaction was stopped with 100 µl/well 12.5% $H_2SO_4$ and read at 450 nm. Out of 96 clones tested, 10 gave signals greater than twice background (background=0.05).

Characterization of a Binding Clone.

Figure 8:
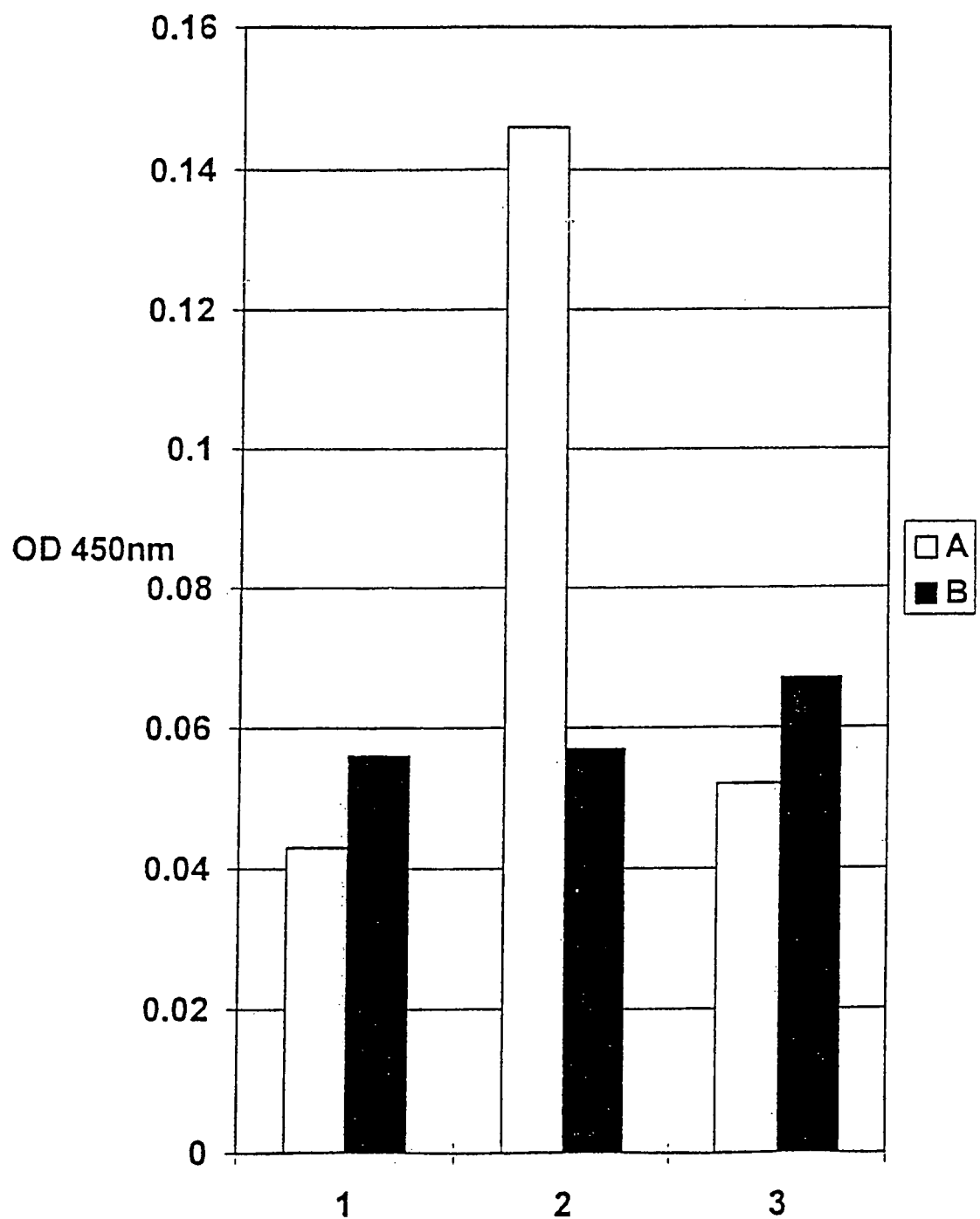
FIG. 8 shows the OD$_{450}$ nm ELISA data for a human scFv PDCP isolated from a human scFv PDCP display library selected against substance P. The PDCP was tested against streptavidin (1), streptavidin-biotinylated substance P (2), and streptavidin-biotinylated CGRP (3), in the presence (B) or absence (A) of free substance P.

A 50-fold concentrated PDCP stock was prepared from a 100 ml amplified culture of a single ELISA positive clone as described above. 10 µl per well of this stock was tested in ELISA as described above for binding to streptavidin, streptavidin-biotinylated-substance P and streptavidin-biotinylated-CGRP (N-terminal biotinylated). Binding was only observed in streptavidin-biotinylated-substance P coated wells indicating that binding was specific. In addition, binding to streptavidin-biotinylated substance P was completely inhibited by incubating the PDCP with 1 µg/ml free substance P (see FIG. 8). The scFv VH (SEQ ID Nos 15 and 16) and VL (SEQ ID Nos 17 and 18) DNA and amino acid sequence was determined by DNA sequencing with oligonucleotides M13REV (SEQ ID No27) and ORSEQFOR (SEQ ID No 36) and is shown in FIG. 9.

The results indicate that target binding activities can be isolated from PDCP display libraries of human scFv fragments.

EXAMPLE 10

In another example the invention provides methods for screening a DNA library whose members require more than one chain for activity, as required by, for example, antibody Fab fragments for ligand binding. To increase the affinity of an antibody of known heavy and light chain sequence, libraries of unknown light chains co-expressed with a known heavy chain are screened for higher affinity antibodies. The known heavy chain antibody DNA sequence is joined to a nucleotide sequence encoding a oestrogen receptor DNA binding domain in a phage vector which does not contain the oestrogen receptor HRE sequence. The antibody DNA sequence for the known heavy chain (VH and CH1) gene is inserted in the 5' region of the oestrogen receptor DBD DNA, behind an appropriate promoter and translation sequences and a sequence encoding a signal peptide leader directing transport of the downstream fusion protein to the periplasmic space. The library of unknown light-chains (VL and CL) is expressed separately from a phagemid expression vector which also contains the oestrogen receptor HRE sequence. Thus when both heavy and light chains are expressed in the same host cell, following infection with the phage containing the heavy chain-DBD fusion, the light chain phagemid vector is preferentially packaged into mature phage particles as single stranded DNA, which is bound by the heavy chain-DBD fusion protein during the packaging process. The light chain proteins are transported to the periplasm where they assemble with the heavy chain that is fused to the DBD protein as it exits the cell on the PDCP. In this example the DBD fusion protein and the HRE DNA sequences are not encoded on the same vector, the unknown peptide sequences are present on the same vector as the HRE sequence. Peptide display carrier packages (PDCP) which encode the protein of interest can then be selected by means of a ligand specific for the antibody.

TABLE 1

(i) Oligonucleotide primers used for human scFv library construction cDNA synthesis primers

| | | |
|---|---|---|
| IgMCDNAFOR | TGGAAGAGGCACGTTCTTTTCTTT | (SEQ ID 38) |
| IgDCDNAFOR | CTCCTTCTTACTCTTGCTGGCGGT | (SEQ ID 37) |
| IgκCDNAFOR | AGACTCTCCCCTGTTGAAGCTCTT | (SEQ ID 39) |
| IgλCDNAFOR | TGAAGATTCTGTAGGGGCCACTGTCTT | (SEQ ID 40) |

JHFOR primers

| | | |
|---|---|---|
| JH1-2FOR | TGAACCGCCTCCACCTGAGGAGACGGTGACCAGGGTGCC | (SEQ ID 41) |
| JH3FOR | TGAACCGCCTCCACCTGAAGAGACGGTGACCATTGTCCC | (SEQ ID 42) |
| JH4-5FOR | TGAACCGCCTCCACCTGAGGAGACGGTGACCAGGGTTCC | (SEQ ID 43) |
| JH6FOR | TGAACCGCCTCCACCTGAGGAGACGGTGACCGTGGTCCC | (SEQ ID 44) |

VH familyBAKprimers

| | | |
|---|---|---|
| VH1BAK | TTTTTGGCCCAGCCGGCCATGGCCCAGGTGCAGCTGGTGCAGTCTGG | (SEQ ID 45) |
| VH2BAK | TTTTTGGCCCAGCCGGCCATGGCCCAGGTCAACTTAAGGGAGTCTGG | (SEQ ID 46) |
| VH3BAK | TTTTTGGCCCAGCCGGCCATGGCCGAGGTGCAGCTGGTGGAGTCTGG | (SEQ ID 47) |
| VH4BAK | TTTTTGGCCCAGCCGGCCATGGCCCAGGTGCAGCTGCAGGAGTCGGG | (SEQ ID 48) |
| VH5BAK | TTTTTGGCCCAGCCGGCCATGGCCGAGGTGCAGCTGTTGCAGTCTGC | (SEQ ID 49) |
| VH6BAK | TTTTTGGCCCAGCCGGCCATGGCCCAGGTACAGCTGCAGCAGTCAGG | (SEQ ID 50) |

Light chain FOR primers

| | | |
|---|---|---|
| SCFVKFOR | TTATTCGCGGCCGCCTAAACAGAGGCAGTTCCAGATTTC | (SEQ ID 51) |
| SCFVλFOR | GTCACTTGCGGCCGCCTACAGTGTGGCCTTGTTGGCTTG | (SEQ ID 52) |

VK family BAK primers

| | | |
|---|---|---|
| VK1BAK | TCTGGCGGTGGCGGATCGGACATCCAGATGACCCAGTCTCC | (SEQ ID 53) |
| VK2BAK | TCTGGCGGTGGCGGATCGGATGTTGTGATGACTCAGTCTCC | (SEQ ID 54) |
| VK3BAK | TCTGGCGGTGGCGGATCGGAAATTGTGTTGACGCAGTCTCC | (SEQ ID 55) |
| VK4BAK | TCTGGCGGTGGCGGATCGGACATCGTGATGACCCAGTCTCC | (SEQ ID 56) |
| VK5BAK | TCTGGCGGTGGCGGATCGGAAACGACACTCACGCAGTCTCC | (SEQ ID 57) |
| VK6BAK | TCTGGCGGTGGCGGATCGGAAATTGTGCTGACTCAGTCTCC | (SEQ ID 58) |

JK FOR primers

| | | |
|---|---|---|
| JK1FOR | TTCTCGTGCGGCCGCCTAACGTTTGATTTCCACCTTGGTCCC | (SEQ ID 59) |
| JK2FOR | TTCTCGTGCGGCCGCCTAACGTTTGATCTCCAGCTTGGTCCC | (SEQ ID 60) |
| JK3FOR | TTCTCGTGCGGCCGCCTAACGTTTGATATCCACTTTGGTCCC | (SEQ ID 61) |
| JK4FOR | TTCTCGTGCGGCCGCCTAACGTTTGATCTCCACCTTGGTCCC | (SEQ ID 62) |
| JK5FOR | TTCTCGTGCGGCCGCCTAACGTTTAATCTCCAGTCGTGTCCC | (SEQ ID 63) |

Vλ family BAK primers

| | | |
|---|---|---|
| Vλ1BAK | TCTGGCGGTGGCGGATCGCAGTCTGTGTTGACGCAGCCGCC | (SEQ ID 64) |
| Vλ2BAK | TCTGGCGGTGGCGGATCGCAGTCTGCCCTGACTCAGCCTGC | (SEQ ID 65) |

TABLE 1-continued (ii) Oligonucleotide primers used for human scFv library construction

| Vλ3aBAK | TCTGGCGGTGGCGGATCGTCCTATGTGCTGACTCAGCCACC | (SEQ ID 66) |
|---|---|---|
| Vλ3bBAK | TCTGGCGGTGGCGGATCGTCTTCTGAGCTGACTCAGGACCC | (SEQ ID 67) |
| Vλ4BAK | TCTGGCGGTGGCGGATCGCACGTTATACTGACTCAACCGCC | (SEQ ID 68) |
| Vλ5BAK | TCTGGCGGTGGCGGATCGCAGGCTGTGCTCACTCAGCCGTC | (SEQ ID 69) |
| Vλ6BAK | TCTGGCGGTGGCGGATCGAATTTTATGCTGACTCAGCCCCA | (SEQ ID 70) |
| Jλ primers | | |
| Jλ1FOR | TTCTCGTGCGGCCGCCTAACCTAGGACGGTGACCTTGGTCCC | (SEQ ID 71) |
| Jλ2-3FOR | TTCTCGTGCGGCCGCCTAACCTAGGACGGTCAGCTTGGTCCC | (SEQ ID 72) |
| Jλ4-5FOR | TTCTCGTGCGGCCGCCTAACCTAAAACGGTGAGCTGGGTCCC | (SEQ ID 73) |
| Linker primers | | |
| LINKAMP3 | CGATCCGCCACCGCCAGA | (SEQ ID 74) |
| LINKAMP5 | GTCTCCTCAGGTGGAGGC | (SEQ ID 75) |
| LINKAMP3T | CGATCCGCCACCGCCAGAGCCACCTCCGCCTGAACCGCCTCCACCTGAGGAGAC | (SEQ ID 76) |

The invention claimed is:

1. A peptide display carrier package (PDCP), said package comprising a recombinant polynucleotide-chimeric protein complex wherein the chimeric protein has a nucleotide binding portion and a target peptide portion, wherein said recombinant polynucleotide comprises a sequence encoding said chimeric protein and a nucleotide sequence motif which is specifically bound by said nucleotide binding portion of said chimeric protein, wherein said nucleotide binding portion comprises a DNA binding domain of an oestrogen or progesterone receptor, and wherein at least the chimeric protein-encoding portion of the recombinant polynucleotide not bound by the chimeric protein nucleotide binding portion is protected by a viral coat protein.

2. A peptide display carrier package (PDCP) as claimed in claim 1, wherein said target peptide portion is displayed externally on the package.

3. A peptide display carrier package (PDCP) as claimed in claim 2 wherein said recombinant polynucleotide includes a linker sequence between the nucleotide sequence encoding the nucleotide binding portion and the nucleotide sequence encoding the target peptide portion.

4. A peptide display carrier package (PDCP) as claimed in claim 3 wherein said recombinant polynucleotide has two or more nucleotide sequence motifs each of which can be bound by the nucleotide binding portion of the chimeric protein.

5. A peptide display carrier package (PDCP) as claimed in claim 4 wherein said recombinant polynucleotide is bound to said chimeric protein as single stranded DNA.

6. A peptide display carrier package (PDCP) as claimed in claim 5 wherein said target peptide portion is located at the N and/or C terminal of the chimeric protein.

7. A peptide display carrier package (PDCP) as claimed in claim 6 which is produced in a host cell transformed with said recombinant polynucleotide and extruded therefrom without lysis of the host cell.

* * * * *

SEQUENCE LISTING

```
<160> NUMBER OF SEQ ID NOS: 78

<210> SEQ ID NO 1
<211> LENGTH: 521
<212> TYPE: DNA
<213> ORGANISM: Recombinant human oestrogen
<220> FEATURE:
<221> NAME/KEY: CDS
<222> LOCATION: (41)..(475)

<400> SEQUENCE: 1
aagcttgcat gcaaattcta tttcaaggag acagtcataa atg aaa tac cta ttg      55
                                             Met Lys Tyr Leu Leu
                                              1               5 cct acg gca gcc gct gga ttg tta tta ctc gcg gcc cag ccg gcc atg     103
Pro Thr Ala Ala Ala Gly Leu Leu Leu Leu Ala Ala Gln Pro Ala Met
            10                  15                  20 gcc caa gtg cag ctg cag taa tag gcg gcc gca ggg gga gga ggg tcc    151
Ala Gln Val Gln Leu Gln      Ala Ala Ala Gly Gly Gly Gly Ser
        25                       30                  35 atg gaa tct gcc aag gag act cgc tac tgt gca gtg tgc aat gac tat    199
Met Glu Ser Ala Lys Glu Thr Arg Tyr Cys Ala Val Cys Asn Asp Tyr
    40                  45                  50 gct tca ggc tac cat tat gga gtc tgg tcc tgt gag ggc tgc aag gcc    247
Ala Ser Gly Tyr His Tyr Gly Val Trp Ser Cys Glu Gly Cys Lys Ala
55                  60                  65 ttc ttc aag aga agt att caa gga cat aac gac tat atg tgt cca gcc    295
Phe Phe Lys Arg Ser Ile Gln Gly His Asn Asp Tyr Met Cys Pro Ala
        70                  75                  80                  85 acc aac cag tgc acc att gat aaa aac agg agg aag agc tgc cag gcc    343
Thr Asn Gln Cys Thr Ile Asp Lys Asn Arg Arg Lys Ser Cys Gln Ala
                90                  95                 100 tgc cgg ctc cgt aaa tgc tac gaa gtg gga atg atg aaa ggt ggg ata    391
Cys Arg Leu Arg Lys Cys Tyr Glu Val Gly Met Met Lys Gly Gly Ile
```

```
              105                 110                 115
cga aaa gac cga aga gga ggg aga atg ttg aaa cac aag cgc cag aga       439
Arg Lys Asp Arg Arg Gly Gly Arg Met Leu Lys His Lys Arg Gln Arg
        120                 125                 130 gat gat ggg gag ggc agg ggt gaa gtg ggg tct tga taatcaggtc            485
Asp Asp Gly Glu Gly Arg Gly Glu Val Gly Ser
        135                 140                 145 agagtgacct gagctaaaat aacacattca gaattc                               521

<210> SEQ ID NO 2
<211> LENGTH: 27
<212> TYPE: PRT
<213> ORGANISM: Recombinant human oestrogen

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln
            20                  25

<210> SEQ ID NO 3
<211> LENGTH: 115
<212> TYPE: PRT
<213> ORGANISM: Recombinant human oestrogen

<400> SEQUENCE: 3

Ala Ala Ala Gly Gly Gly Gly Ser Met Glu Ser Ala Lys Glu Thr Arg
1               5                   10                  15

Tyr Cys Ala Val Cys Asn Asp Tyr Ala Ser Gly Tyr His Tyr Gly Val
            20                  25                  30

Trp Ser Cys Glu Gly Cys Lys Ala Phe Phe Lys Arg Ser Ile Gln Gly
        35                  40                  45

His Asn Asp Tyr Met Cys Pro Ala Thr Asn Gln Cys Thr Ile Asp Lys
    50                  55                  60

Asn Arg Arg Lys Ser Cys Gln Ala Cys Arg Leu Arg Lys Cys Tyr Glu
65                  70                  75                  80

Val Gly Met Met Lys Gly Gly Ile Arg Lys Asp Arg Arg Gly Gly Arg
                85                  90                  95

Met Leu Lys His Lys Arg Gln Arg Asp Asp Gly Glu Gly Arg Gly Glu
            100                 105                 110

Val Gly Ser
        115

<210> SEQ ID NO 4
<211> LENGTH: 102
<212> TYPE: DNA
<213> ORGANISM: human
<220> FEATURE:
<221> NAME/KEY: CDS
<222> LOCATION: (1)..(102)

<400> SEQUENCE: 4 aaa cga act gtg gct gca cca tct gtc ttc atc ttc ccg cca tct gat       48
Lys Arg Thr Val Ala Ala Pro Ser Val Phe Ile Phe Pro Pro Ser Asp
1               5                   10                  15 gag cag ttg aaa tct gga act gcc tct gtt gtg tgc ctg ctg aat aac       96
Glu Gln Leu Lys Ser Gly Thr Ala Ser Val Val Cys Leu Leu Asn Asn
            20                  25                  30 ttc tat                                                              102
Phe Tyr
```

-continued

```
<210> SEQ ID NO 5
<211> LENGTH: 34
<212> TYPE: PRT
<213> ORGANISM: human

<400> SEQUENCE: 5

Lys Arg Thr Val Ala Ala Pro Ser Val Phe Ile Phe Pro Pro Ser Asp
 1               5                  10                  15

Glu Gln Leu Lys Ser Gly Thr Ala Ser Val Val Cys Leu Leu Asn Asn
        20                  25                  30

Phe Tyr

<210> SEQ ID NO 6
<211> LENGTH: 150
<212> TYPE: DNA
<213> ORGANISM: Human lymphocyte
<220> FEATURE:
<221> NAME/KEY: CDS
<222> LOCATION: (1)..(150)

<400> SEQUENCE: 6 atg gcc cag ccc acc acg cgt ccg ggc caa ggg aca cga ctg gac att      48
Met Ala Gln Pro Thr Thr Arg Pro Gly Gln Gly Thr Arg Leu Asp Ile
 1               5                  10                  15 aaa cga act gtg gct gca cca tct gtc ttc atc ttc ccg cca tct gat      96
Lys Arg Thr Val Ala Ala Pro Ser Val Phe Ile Phe Pro Pro Ser Asp
                20                  25                  30 gag cag ttg aaa tct gga act gcc tct gtt gtg tgc ctg ctg aat aac     144
Glu Gln Leu Lys Ser Gly Thr Ala Ser Val Val Cys Leu Leu Asn Asn
            35                  40                  45 ttc tat                                                             150
Phe Tyr
    50

<210> SEQ ID NO 7
<211> LENGTH: 50
<212> TYPE: PRT
<213> ORGANISM: Human lymphocyte

<400> SEQUENCE: 7

Met Ala Gln Pro Thr Thr Arg Pro Gly Gln Gly Thr Arg Leu Asp Ile
 1               5                  10                  15

Lys Arg Thr Val Ala Ala Pro Ser Val Phe Ile Phe Pro Pro Ser Asp
                20                  25                  30

Glu Gln Leu Lys Ser Gly Thr Ala Ser Val Val Cys Leu Leu Asn Asn
            35                  40                  45

Phe Tyr
    50

<210> SEQ ID NO 8
<211> LENGTH: 150
<212> TYPE: DNA
<213> ORGANISM: Human lymphocyte
<220> FEATURE:
<221> NAME/KEY: CDS
<222> LOCATION: (1)..(150)

<400> SEQUENCE: 8 atg gcc cag tcc cac cac gcg tcc ggc gga ggg acc aag gtg gag atc      48
Met Ala Gln Ser His His Ala Ser Gly Gly Gly Thr Lys Val Glu Ile
 1               5                  10                  15 aaa cga act gtg gct gca cca tct gtc ttc atc ttc ccg cca tct gat      96
Lys Arg Thr Val Ala Ala Pro Ser Val Phe Ile Phe Pro Pro Ser Asp
```

```
                   20                  25                  30
gag cag ttg aaa tct gga act gcc tct gtt gtg tgc ctg ctg aat aac      144
Glu Gln Leu Lys Ser Gly Thr Ala Ser Val Val Cys Leu Leu Asn Asn
         35                  40                  45 ttc tat                                                              150
Phe Tyr
     50

<210> SEQ ID NO 9
<211> LENGTH: 50
<212> TYPE: PRT
<213> ORGANISM: Human lymphocyte

<400> SEQUENCE: 9

Met Ala Gln Ser His His Ala Ser Gly Gly Gly Thr Lys Val Glu Ile
  1               5                  10                  15

Lys Arg Thr Val Ala Ala Pro Ser Val Phe Ile Phe Pro Pro Ser Asp
                 20                  25                  30

Glu Gln Leu Lys Ser Gly Thr Ala Ser Val Val Cys Leu Leu Asn Asn
         35                  40                  45

Phe Tyr
     50

<210> SEQ ID NO 10
<211> LENGTH: 566
<212> TYPE: DNA
<213> ORGANISM: Recombinant human oestrogen
<220> FEATURE:
<221> NAME/KEY: CDS
<222> LOCATION: (41)..(475)

<400> SEQUENCE: 10
aagcttgcat gcaaattcta tttcaaggag acagtcataa atg aaa tac cta ttg       55
                                             Met Lys Tyr Leu Leu
                                               1               5 cct acg gca gcc gct gga ttg tta tta ctc gcg gcc cag ccg gcc atg     103
Pro Thr Ala Ala Ala Gly Leu Leu Leu Leu Ala Ala Gln Pro Ala Met
             10                  15                  20 gcc gag gtg caa ctg cag taa tag gcg gcc gca ggg gga gga ggg tcc     151
Ala Glu Val Gln Leu Gln          Ala Ala Ala Gly Gly Gly Gly Ser
                 25                      30                  35 atg gaa tct gcc aag gag act cgc tac tgt gca gtg tgc aat gac tat     199
Met Glu Ser Ala Lys Glu Thr Arg Tyr Cys Ala Val Cys Asn Asp Tyr
         40                  45                  50 gct tca ggc tac cat tat gga gtc tgg tcc tgt gag ggc tgc aag gcc     247
Ala Ser Gly Tyr His Tyr Gly Val Trp Ser Cys Glu Gly Cys Lys Ala
 55                  60                  65 ttc ttc aag aga agt att caa gga cat aac gac tat atg tgt cca gcc     295
Phe Phe Lys Arg Ser Ile Gln Gly His Asn Asp Tyr Met Cys Pro Ala
         70                  75                  80                  85 acc aac cag tgc acc att gat aaa aac agg agg aag agc tgc cag gcc     343
Thr Asn Gln Cys Thr Ile Asp Lys Asn Arg Arg Lys Ser Cys Gln Ala
                 90                  95                 100 tgc cgg ctc cgt aaa tgc tac gaa gtg gga atg atg aaa ggt ggg ata     391
Cys Arg Leu Arg Lys Cys Tyr Glu Val Gly Met Met Lys Gly Gly Ile
            105                 110                 115 cga aaa gac cga aga gga ggg aga atg ttg aaa cac aag cgc cag aga     439
Arg Lys Asp Arg Arg Gly Gly Arg Met Leu Lys His Lys Arg Gln Arg
        120                 125                 130 gat gat ggg gag ggc agg ggt gaa gtg ggg tct tga taatcaggtc          485
Asp Asp Gly Glu Gly Arg Gly Glu Val Gly Ser
135                 140                 145
```

```
agagtgacct gagctaaaat aacacattca ggtcgacttg ggtcagtctg accgggacaa      545
agttaatgta acctcgaatt c                                                 566

<210> SEQ ID NO 11
<211> LENGTH: 27
<212> TYPE: PRT
<213> ORGANISM: Recombinant human oestrogen

<400> SEQUENCE: 11

Met Lys Tyr Leu Leu Pro Thr Ala Ala Gly Leu Leu Leu Ala
  1               5                  10                  15

Ala Gln Pro Ala Met Ala Glu Val Gln Leu Gln
                 20                  25

<210> SEQ ID NO 12
<211> LENGTH: 115
<212> TYPE: PRT
<213> ORGANISM: Recombinant human oestrogen

<400> SEQUENCE: 12

Ala Ala Ala Gly Gly Gly Gly Ser Met Glu Ser Ala Lys Glu Thr Arg
  1               5                  10                  15

Tyr Cys Ala Val Cys Asn Asp Tyr Ala Ser Gly Tyr His Tyr Gly Val
                 20                  25                  30

Trp Ser Cys Glu Gly Cys Lys Ala Phe Phe Lys Arg Ser Ile Gln Gly
             35                  40                  45

His Asn Asp Tyr Met Cys Pro Ala Thr Asn Gln Cys Thr Ile Asp Lys
         50                  55                  60

Asn Arg Arg Lys Ser Cys Gln Ala Cys Arg Leu Arg Lys Cys Tyr Glu
 65                  70                  75                  80

Val Gly Met Met Lys Gly Gly Ile Arg Lys Asp Arg Arg Gly Gly Arg
                 85                  90                  95

Met Leu Lys His Lys Arg Gln Arg Asp Asp Gly Glu Gly Arg Gly Glu
                100                 105                 110

Val Gly Ser
        115

<210> SEQ ID NO 13
<211> LENGTH: 539
<212> TYPE: DNA
<213> ORGANISM: Recombinant human oestrogen
<220> FEATURE:
<221> NAME/KEY: CDS
<222> LOCATION: (41)..(478)

<400> SEQUENCE: 13
aagcttgcat gcaaattcta tttcaaggag acagtcataa atg aaa tac cta ttg       55
                                             Met Lys Tyr Leu Leu
                                              1               5 cct acg gca gcc gct gga ttg tta tta ctc gcg gcc cag ccg gca atg     103
Pro Thr Ala Ala Ala Gly Leu Leu Leu Leu Ala Ala Gln Pro Ala Met
                 10                  15                  20 gcc gag atg gaa tct gcc aag gag act cgc tac tgt gca gtg tgc aat     151
Ala Glu Met Glu Ser Ala Lys Glu Thr Arg Tyr Cys Ala Val Cys Asn
             25                  30                  35 gac tat gct tca ggc tac cat tat gga gtc tgg tcc tgt gag ggc tgc     199
Asp Tyr Ala Ser Gly Tyr His Tyr Gly Val Trp Ser Cys Glu Gly Cys
         40                  45                  50 aag gcc ttc ttc aag aga agt att caa gga cat aac gac tat atg tgt     247
Lys Ala Phe Phe Lys Arg Ser Ile Gln Gly His Asn Asp Tyr Met Cys
```

```
                55                  60                  65
cca gcc acc aac cag tgc acc att gat aaa aac agg agg aag agc tgc        295
Pro Ala Thr Asn Gln Cys Thr Ile Asp Lys Asn Arg Arg Lys Ser Cys
 70                  75                  80                  85 cag gcc tgc cgg ctc cgt aaa tgc tac gaa gtg gga atg atg aaa ggt        343
Gln Ala Cys Arg Leu Arg Lys Cys Tyr Glu Val Gly Met Met Lys Gly
                 90                  95                 100 ggg ata cga aaa gac cga aga gga ggt aga atg ttg aaa cac aag cgc        391
Gly Ile Arg Lys Asp Arg Arg Gly Gly Arg Met Leu Lys His Lys Arg
            105                 110                 115 cag aga gat gat ggg gag ggc agg ggt gaa gtg ggg tct ggg gga gga        439
Gln Arg Asp Asp Gly Glu Gly Arg Gly Glu Val Gly Ser Gly Gly Gly
        120                 125                 130 ggg tcg gcc cag ccg gcc ctc ctg cag ctg gcg gcc gca taactgattg         488
Gly Ser Ala Gln Pro Ala Leu Leu Gln Leu Ala Ala Ala
    135                 140                 145 agtcgacttg ggtcagtctg accgggacaa agttaatgta acctcgaatt c               539

<210> SEQ ID NO 14
<211> LENGTH: 146
<212> TYPE: PRT
<213> ORGANISM: Recombinant human oestrogen

<400> SEQUENCE: 14

Met Lys Tyr Leu Leu Pro Thr Ala Ala Ala Gly Leu Leu Leu Leu Ala
  1               5                  10                  15

Ala Gln Pro Ala Met Ala Glu Met Glu Ser Ala Lys Glu Thr Arg Tyr
                 20                  25                  30

Cys Ala Val Cys Asn Asp Tyr Ala Ser Gly Tyr His Tyr Gly Val Trp
             35                  40                  45

Ser Cys Glu Gly Cys Lys Ala Phe Phe Lys Arg Ser Ile Gln Gly His
         50                  55                  60

Asn Asp Tyr Met Cys Pro Ala Thr Asn Gln Cys Thr Ile Asp Lys Asn
 65                  70                  75                  80

Arg Arg Lys Ser Cys Gln Ala Cys Arg Leu Arg Lys Cys Tyr Glu Val
                 85                  90                  95

Gly Met Met Lys Gly Gly Ile Arg Lys Asp Arg Arg Gly Gly Arg Met
            100                 105                 110

Leu Lys His Lys Arg Gln Arg Asp Asp Gly Glu Gly Arg Gly Glu Val
        115                 120                 125

Gly Ser Gly Gly Gly Ser Ala Gln Pro Ala Leu Leu Gln Leu Ala
    130                 135                 140

Ala Ala
145

<210> SEQ ID NO 15
<211> LENGTH: 372
<212> TYPE: DNA
<213> ORGANISM: Human
<220> FEATURE:
<221> NAME/KEY: CDS
<222> LOCATION: (1)..(372)

<400> SEQUENCE: 15 cag gta cag ctg cag cag tca ggg gga ggc gtg gtc cag cct ggg agg         48
Gln Val Gln Leu Gln Gln Ser Gly Gly Gly Val Val Gln Pro Gly Arg
  1               5                  10                  15 tcc ctg aga ctc tcc tgt gca gcc tcg gga ttc ccc ttt agt act tat         96
Ser Leu Arg Leu Ser Cys Ala Ala Ser Gly Phe Pro Phe Ser Thr Tyr
                 20                  25                  30
```

```
ggc atg cac tgg cgc cag gct gtc cca ggc aag ggg ctg gag tgg gtg      144
Gly Met His Trp Arg Gln Ala Val Pro Gly Lys Gly Leu Glu Trp Val
        35                  40                  45 gca gtt ata tca tat gat gga agt aat aaa tac tac gca gac tcc gtg      192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ttg tat      240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt      288
Leu Gln Met Asn Ser Leu Arg Ala Glu Asp Thr Ala Val Tyr Tyr Cys
                85                  90                  95 gcg aga gat tta gac ccc acc agg tat agc agt ggc tgg gac act gac      336
Ala Arg Asp Leu Asp Pro Thr Arg Tyr Ser Ser Gly Trp Asp Thr Asp
            100                 105                 110 tac tgg ggc cag ggg cac ctg gtc act gtc tcc tca                      372
Tyr Trp Gly Gln Gly His Leu Val Thr Val Ser Ser
        115                 120
```

```
<210> SEQ ID NO 16
<211> LENGTH: 124
<212> TYPE: PRT
<213> ORGANISM: Human

<400> SEQUENCE: 16

Gln Val Gln Leu Gln Gln Ser Gly Gly Gly Val Val Gln Pro Gly Arg
1               5                   10                  15

Ser Leu Arg Leu Ser Cys Ala Ala Ser Gly Phe Pro Phe Ser Thr Tyr
            20                  25                  30

Gly Met His Trp Arg Gln Ala Val Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Asp Pro Thr Arg Tyr Ser Ser Gly Trp Asp Thr Asp
            100                 105                 110

Tyr Trp Gly Gln Gly His Leu Val Thr Val Ser Ser
        115                 120
```

```
<210> SEQ ID NO 17
<211> LENGTH: 327
<212> TYPE: DNA
<213> ORGANISM: Human
<220> FEATURE:
<221> NAME/KEY: CDS
<222> LOCATION: (1)..(327)

<400> SEQUENCE: 17 gaa acg aca ctc acg cag tct cca ggc acc ctg tct ttg tct ccg ggg       48
Glu Thr Thr Leu Thr Gln Ser Pro Gly Thr Leu Ser Leu Ser Pro Gly
1               5                   10                  15 gaa aga gcc acc ctc tcc tgc agg gcc agt cag aat att ggc agc agc       96
Glu Arg Ala Thr Leu Ser Cys Arg Ala Ser Gln Asn Ile Gly Ser Ser
            20                  25                  30 tcc tta gcc tgg tac caa cag aaa cct ggc cag gct ccc agg ctc ctc      144
Ser Leu Ala Trp Tyr Gln Gln Lys Pro Gly Gln Ala Pro Arg Leu Leu
        35                  40                  45
```

```
atc tat ggt gca tcc acc agg gcc act ggt atc cca gcc agg ttc agt      192
Ile Tyr Gly Ala Ser Thr Arg Ala Thr Gly Ile Pro Ala Arg Phe Ser
 50                  55                  60 ggc agt ggg tca ggg aca caa ttc act ctc acc atc agc agc ctg cag      240
Gly Ser Gly Ser Gly Thr Gln Phe Thr Leu Thr Ile Ser Ser Leu Gln
 65                  70                  75                  80 tct gaa gat ttt gca gtt tat tac tgt cag cag tat aat ttc tgg cca      288
Ser Glu Asp Phe Ala Val Tyr Tyr Cys Gln Gln Tyr Asn Phe Trp Pro
                 85                  90                  95 ttc act ttt ggc cct ggg acc aag ctg gag atc aaa cgt                  327
Phe Thr Phe Gly Pro Gly Thr Lys Leu Glu Ile Lys Arg
                100                 105

<210> SEQ ID NO 18
<211> LENGTH: 109
<212> TYPE: PRT
<213> ORGANISM: Human

<400> SEQUENCE: 18

Glu Thr Thr Leu Thr Gln Ser Pro Gly Thr Leu Ser Leu Ser Pro Gly
  1               5                  10                  15

Glu Arg Ala Thr Leu Ser Cys Arg Ala Ser Gln Asn Ile Gly Ser Ser
             20                  25                  30

Ser Leu Ala Trp Tyr Gln Gln Lys Pro Gly Gln Ala Pro Arg Leu Leu
         35                  40                  45

Ile Tyr Gly Ala Ser Thr Arg Ala Thr Gly Ile Pro Ala Arg Phe Ser
 50                  55                  60

Gly Ser Gly Ser Gly Thr Gln Phe Thr Leu Thr Ile Ser Ser Leu Gln
 65                  70                  75                  80

Ser Glu Asp Phe Ala Val Tyr Tyr Cys Gln Gln Tyr Asn Phe Trp Pro
                 85                  90                  95

Phe Thr Phe Gly Pro Gly Thr Lys Leu Glu Ile Lys Arg
                100                 105

<210> SEQ ID NO 19
<211> LENGTH: 72
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 19
ttttctgcag taataggcgg ccgcaggggg aggagggtcc atcgaaggtc gcgaagcaga     60
gactgttgaa ag                                                        72

<210> SEQ ID NO 20
<211> LENGTH: 75
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 20
ttttgaattc ttattaacca ccgaactgcg ggtgacgcca agcgcttgcg gccgttaaga     60
ctccttatta cgcag                                                     75

<210> SEQ ID NO 21
<211> LENGTH: 32
<212> TYPE: DNA
<213> ORGANISM: Artificial Sequence
```

```
<220> FEATURE:
<223> OTHER INFORMATION: Description of Artificial Sequence:
      synthetic DNA

<400> SEQUENCE: 21
aaaagcggcc gcactggcct gagagannnn nn                                32

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 22
tcgacccacg cgtccg                                                  16

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 23
gggtgccgag gc                                                      12

<210> SEQ ID NO 24
<211> LENGTH: 72
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 24
aaaagaattc tgaatgtgtt attttagctc aggtcactct gacctgatta tcaagacccc  60
acttcacccc ct                                                      72

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 25
aaaagcggcc gcaggggagg gagggtccat ggaatctgcc aaggag                 46

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 26
gtaaaacgac ggccagt                                                 17

<210> SEQ ID NO 27
<211> LENGTH: 20
<212> TYPE: DNA
<213> ORGANISM: Artificial Sequence
```

```
<220> FEATURE:
<223> OTHER INFORMATION: Description of Artificial Sequence:
      synthetic DNA

<400> SEQUENCE: 27
ggataacaat ttcacacagg                                                    20

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 28
aaagcggccg cactggcctg agaga                                              25

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 29
aaaaggccca gccggccatg gcccagccca ccacgcgtcc g                            41

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 30
aaaaggccca gccggccatg gcccagtccc accacgcgtc cg                           42

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 31
aaaaggccca gccggccatg gcccagtacc caccacgcgt ccg                          43

<210> SEQ ID NO 32
<211> LENGTH: 72
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 32
aaaagaattc gaggttacat taactttgtt ccggtcagac tgacccaagt cgacctgaat        60
gtgttatttt ag                                                            72

<210> SEQ ID NO 33
<211> LENGTH: 32
<212> TYPE: DNA
<213> ORGANISM: Artificial Sequence
```

<220> FEATURE:
<223> OTHER INFORMATION: Description of Artificial Sequence:
      synthetic DNA

<400> SEQUENCE: 33
ccttggcaga ttccatctcg gccattgccg gc                              32

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 34
ccggcaatgg ccgagatgga atctgccaag g                               31

<210> SEQ ID NO 35
<211> LENGTH: 86
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 35
ttttgtcgac tcaatcagtt atgcggccgc cagctgcagg agggccggct gggccgaccc    60
tcctccccca gaccccactt cacccc                                        86

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 36
tgttgaaaca caagcgccag                                            20

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 37
tggaagaggc acgttctttt cttt                                       24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 38
ctccttctta ctcttgctgg cggt                                       24

<210> SEQ ID NO 39
<211> LENGTH: 24
<212> TYPE: DNA
<213> ORGANISM: Artificial Sequence

```
<220> FEATURE:
<223> OTHER INFORMATION: Description of Artificial Sequence:
      synthetic DNA

<400> SEQUENCE: 39
agatctcccc ctgttgaagc tctt                                              24

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 40
tgaagattct gtagggggcca ctgtctt                                          27

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 41
tgaaccgcct ccacctgagg agacggtgac cagggtgcc                              39

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 42
tgaaccgcct ccacctgaag agacggtgac cattgtccc                              39

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 43
tgaaccgcct ccacctgagg agacggtgac cagggttcc                              39

<210> SEQ ID NO 44
<211> LENGTH: 39
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 44
tgaaccgcct ccacctgagg agacggtgac cgtggtccc                              39

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence:
```

```
synthetic DNA

<400> SEQUENCE: 45
tttttggccc agccggccat ggcccaggtg cagctggtgc agtctgg                47

<210> SEQ ID NO 46
<211> LENGTH: 47
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 46
tttttggccc agccggccat ggcccaggtc aacttaaggg agtctgg                47

<210> SEQ ID NO 47
<211> LENGTH: 47
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 47
tttttggccc agccggccat ggccgaggtg cagctggtgg agtctgg                47

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 48
tttttggccc agccggccat ggcccaggtg cagctgcagg agtcggg                47

<210> SEQ ID NO 49
<211> LENGTH: 47
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 49
tttttggccc agccggccat ggccgaggtg cagctgttgc agtctgc                47

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 50
tttttggccc agccggccat ggcccaggta cagctgcagc agtcagg                47

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence:
      synthetic DNA
```

```
<400> SEQUENCE: 51
ttattcgcgg ccgcctaaac agaggcagtt ccagatttc                                39

<210> SEQ ID NO 52
<211> LENGTH: 39
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 52
gtcacttgcg gccgcctaca gtgtggcctt gttggcttg                                39

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 53
tctggcggtg gcggatcgga catccagatg acccagtctc c                             41

<210> SEQ ID NO 54
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 54
tctggcggtg gcggatcgga tgttgtgatg actcagtctc c                             41

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 55
tctggcggtg gcggatcgga aattgtgttg acgcagtctc c                             41

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 56
tctggcggtg gcggatcgga catcgtgatg acccagtctc c                             41

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 57
```
tctggcggtg gcggatcgga aacgacactc acgcagtctc c    41

<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 58
tctggcggtg gcggatcgga aattgtgctg actcagtctc c    41

<210> SEQ ID NO 59
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 59
ttctcgtgcg gccgcctaac gtttgatttc caccttggtc cc    42

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 60
ttctcgtgcg gccgcctaac gtttgatctc cagcttggtc cc    42

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 61
ttctcgtgcg gccgcctaac gtttgatatc cactttggtc cc    42

<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 62
ttctcgtgcg gccgcctaac gtttgatctc caccttggtc cc    42

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 63
ttctcgtgcg gccgcctaac gtttaatctc cagtcgtgtc cc    42

-continued

<210> SEQ ID NO 64
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 64
tctggcggtg gcggatcgca gtctgtgttg acgcagccgc c            41

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 65
tctggcggtg gcggatcgca gtctgccctg actcagcctg c            41

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 66
tctggcggtg gcggatcgtc ctatgtgctg actcagccac c            41

<210> SEQ ID NO 67
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 67
tctggcggtg gcggatcgtc ttctgagctg actcaggacc c            41

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 68
tctggcggtg gcggatcgca cgttatactg actcaaccgc c            41

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 69
tctggcggtg gcggatcgca ggctgtgctc actcagccgt c            41

<210> SEQ ID NO 70

```
<211> LENGTH: 41
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 70
tctggcggtg gcggatcgaa ttttatgctg actcagcccc a                    41

<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 71
ttctcgtgcg gccgcctaac ctaggacggt gaccttggtc cc                   42

<210> SEQ ID NO 72
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 72
ttctcgtgcg gccgcctaac ctaggacggt cagcttggtc cc                   42

<210> SEQ ID NO 73
<211> LENGTH: 42
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 73
ttctcgtgcg gccgcctaac ctaaaacggt gagctgggtc cc                   42

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 74
cgatccgcca ccgccaga                                              18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 75
gtctcctcag gtggaggc                                              18

<210> SEQ ID NO 76
<211> LENGTH: 54
<212> TYPE: DNA
```

```
<213> ORGANISM: Artificial Sequence
<220> FEATURE:
<223> OTHER INFORMATION: Description of Artificial Sequence:
      synthetic DNA

<400> SEQUENCE: 76
cgatccgcca ccgccagagc cacctccgcc tgaaccgcct ccacctgagg agac        54

<210> SEQ ID NO 77
<211> LENGTH: 38
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 77
tcaggtcaga gtgacctgag ctaaaataac acattcag                          38

<210> SEQ ID NO 78
<211> LENGTH: 38
<212> TYPE: DNA
<213> ORGANISM: Artificial Sequence
<220> FEATURE:
<223> OTHER INFORMATION: Description of Artificial Sequence:
      synthetic DNA

<400> SEQUENCE: 78
agtccagtct cactggactc gattttattg tgtaagtc                          38
```